(12) United States Patent
Holland et al.

(10) Patent No.: US 10,894,956 B2
(45) Date of Patent: Jan. 19, 2021

(54) PHOSPHOLIPID NANOGEL FOR EXOGLYCOSIDASE ENZYME STABILIZATION

(71) Applicant: West Virginia University, Morgantown, WV (US)

(72) Inventors: Lisa Holland, Morgantown, WV (US); Srikanth Gattu, Morgantown, WV (US)

(73) Assignee: West Virginia University, Morgantown, WV (US)

( * ) Notice: Subject to any disclaimer, the term of this patent is extended or adjusted under 35 U.S.C. 154(b) by 4 days.

(21) Appl. No.: 15/911,624

(22) Filed: Mar. 5, 2018

(65) Prior Publication Data

US 2018/0251752 A1    Sep. 6, 2018

Related U.S. Application Data

(60) Provisional application No. 62/467,072, filed on Mar. 3, 2017.

(51) Int. Cl.
| | |
|---|---|
| C12N 9/96 | (2006.01) |
| C12N 9/24 | (2006.01) |
| C07F 9/10 | (2006.01) |
| C11C 3/06 | (2006.01) |
| C11C 3/10 | (2006.01) |
| B81B 1/00 | (2006.01) |
| B82Y 30/00 | (2011.01) |

(52) U.S. Cl.
CPC ............... *C12N 9/96* (2013.01); *B81B 1/006* (2013.01); *B82Y 30/00* (2013.01); *C07F 9/10* (2013.01); *C07F 9/106* (2013.01); *C11C 3/06* (2013.01); *C11C 3/10* (2013.01); *C12N 9/2402* (2013.01)

(58) Field of Classification Search
None
See application file for complete search history.

(56) References Cited

U.S. PATENT DOCUMENTS

| 2003/0044455 A1* | 3/2003 | Kazakov | A61K 9/127 424/450 |
|---|---|---|---|
| 2007/0209941 A1* | 9/2007 | Holland | B01L 3/502738 204/601 |

OTHER PUBLICATIONS

Luo et al. Anal Chem. Feb. 15, 2010;82(4):1228-33 (Year: 2010).*
Holland et al. Tunable selectivity through nanogel enhanced microscale separations. Abstracts of Papers, 248th ACS National Meeting & Exposition, San Francisco, CA, United States, Aug. 10-14, 2014 (2014), ANYL-60. American Chemical Society: Washington, D. C. (Year: 2014).*
Sanda et al. Molecular & Cellular Proteomics (2013), 12(5), 1294-1305 (Year: 2013).*

* cited by examiner

*Primary Examiner* — Christian L Fronda
(74) *Attorney, Agent, or Firm* — Thomas|Horstemeyer LLP

(57) ABSTRACT

Described herein are phospholipid nanogels that can contain a low concentration (less than about 250 μUnits/μL) of an exoglycosidase enzyme. Also described herein are systems and devices that can contain a phospholipid nanogel that can contain a low concentration (less than about 250 μUnits/μL) of an exoglycosidase enzyme. Also described herein are methods of using the phospholipid nanogels described herein and devices and systems that can contain a phospholipid nanogel described herein.

5 Claims, 18 Drawing Sheets

3' substrate product

6' substrate

| Time, s | static,[b] μM/s | mixed,[c] μM/s |
|---|---|---|
| 40 | 13.9 ± 0.6 | 9.9 ± 0.9 |
| 60 | 11.6 ± 0.3 | 9.5 ± 0.5 |
| 100 | 8.4 ± 0.3 | 8.5 ± 0.4 |
| 200 | 7.3 ± 0.1 | 8.4 ± 0.5 |
| Ave[d] | 10 ± 3 (30%) | 9.1 ± 0.7 (9%) |

FIG. 8

|  | α2-3,6,8,9 neuraminidase | | α2-3 neuraminidase[4] |
| --- | --- | --- | --- |
|  | 3'-sialyllactose[2] | 6'-sialyllactose[3] | 3'-sialyllactose[3] |
| $K_M \pm s.d.$ (mM) | 3.3 ± 0.8 | 2 ± 1 | 3 ± 2 |
| $V_{max} \pm s.d.$ (µM/min) | 2100 ± 200 | 400 ± 100 | 900 ± 300 |

FIG. 13

PHOSPHOLIPID NANOGEL FOR EXOGLYCOSIDASE ENZYME STABILIZATION

CROSS-REFERENCE TO RELATED APPLICATIONS

This application claims the benefit of and priority to U.S. Provisional Patent Application No. 62/467,072, filed on Mar. 3, 2017, entitled "Phospholipid Nanogel for Enzyme Stabilization," the contents of which is incorporated by reference herein in its entirety.

STATEMENT REGARDING FEDERALLY SPONSORED RESEARCH OR DEVELOPMENT

This invention was made with government support under grant number R01GM114330 awarded by the National Institutes of Health and grant number CHE1212537 awarded by the National Science Foundation. The government has certain rights in the invention.

BACKGROUND

Exoglycosidase enzymes are used in many assays and reactions. However, exoglycosidase enzymes loose activity when present in low concentrations in free solutions and/or immobilized on surface. Thus there exists a need for improved techniques and methods for preserving exoglycosidase activity when present in low concentrations.

SUMMARY

Described in various embodiments herein are phospholipid nanogels that can include an amount of 1,2-dimyristoyl-sn-glycero-3-phosphocholine (DMPC); an amount of 1,2-dihexanoyl-sn-glycero-3-phosphocholine (DHPC); and an amount of an exoglycosidase enzyme that can range from about 0.001 µUnits/µL of the phospholipid nanogel to about 250 µUnits/µL of the phospholipid nanogel. The ratio of DMPC to DHPC can range from about 2.0 to about 3.0. The exoglycosidase enzyme can be selected from the group of: α1-2 Fucosidase, α1-6 Fucosidase, α1-2 Mannosidase, α1-2,3 Mannosidase, α1-2,3,4,6 Fucosidase, α1-2,3,6 Mannosidase, α1-2,4,6 Fucosidase, α1-2,4,6 Fucosidase O, α1-3,4 Fucosidase, α1-3,4,6 Galactosidase, α1-3,6 Galactosidase, α1-6 Mannosidase, α2-3 Neuraminidase, α2-3 Neuraminidase S, α2-3,6 Neuraminidase, α2-3,6,8 Neuraminidase, α2-3,6,8,9 Neuraminidase, α2-3,6,8,9 Neuraminidase A, α-N-Acetylgalactosaminidase, β1-3 Galactosidase, β1-3,6 Galactosidase, β1-4,6 Galactosidase, β1-3,4 Galactosidase, β1-4 Galactosidase, β1-4 Galactosidase S, β-1-2,3,4,6-N-Acetylglucosaminidase, β-N-Acetylglucosaminidase S, β-N-Acetylhexosaminidase and any combination thereof. The phospholipid nanogel can be temperature responsive. The phospholipid nanogel can have a gel transition temperature of about 23° C. The pH of the phospholipid nanogel can range from about 4 to about 8. The phospholipid nanogel can further include a reagent selected from the group of: sodium phosphate, potassium phosphate, citric acid, 2-morpholin-4-ylethanesulfonic acid, 3-(N-Morpholino)propanesulfonic acid, sodium acetate, ammonium acetate, calcium, magnesium, sodium azide, mM ethylenediaminetetraacetic acid, and any combination thereof.

Also described in various embodiments herein are devices that can include a phospholipid nanogel having an amount of 1,2-dimyristoyl-sn-glycero-3-phosphocholine (DMPC); an amount of 1,2-dihexanoyl-sn-glycero-3-phosphocholine (DHPC); and an amount of an exoglycosidase enzyme that can range from about 0.001 µUnits/µL of the phospholipid nanogel to about 250 µUnits/µL of the phospholipid nanogel. The ratio of DMPC to DHPC in the phospholipid nanogel can range from about 2.0 to about 3.0. The exoglycosidase enzyme can be selected from the group of: α1-2 Fucosidase, α1-6 Fucosidase, α1-2 Mannosidase, α1-2,3 Mannosidase, α1-2,3,4,6 Fucosidase, α1-2,3,6 Mannosidase, α1-2,4,6 Fucosidase, α1-2,4,6 Fucosidase O, α1-3,4 Fucosidase, α1-3,4,6 Galactosidase, α1-3,6 Galactosidase, α1-6 Mannosidase, α2-3 Neuraminidase, α2-3 Neuraminidase S, α2-3,6 Neuraminidase, α2-3,6,8 Neuraminidase, α2-3,6,8,9 Neuraminidase, α2-3,6,8,9 Neuraminidase A, α-N-Acetylgalactosaminidase, β1-3 Galactosidase, β1-3,6 Galactosidase, β1-4,6 Galactosidase, β1-3,4 Galactosidase, β1-4 Galactosidase, β1-4 Galactosidase S, β-1-2,3,4,6-N-Acetylglucosaminidase, β-N-Acetylglucosaminidase S, β-N-Acetylhexosaminidase and any combination thereof. The phospholipid nanogel can be temperature responsive. The phospholipid nanogel can have a gel transition temperature of about 23° C. The pH of the phospholipid nanogel can range from about 4 to about 8. The phospholipid nanogel can further include a reagent selected from the group of: sodium phosphate, potassium phosphate, citric acid, 2-morpholin-4-ylethanesulfonic acid, 3-(N-Morpholino)propanesulfonic acid, sodium acetate, ammonium acetate, calcium, magnesium, sodium azide, mM ethylenediaminetetraacetic acid, and any combination thereof. The device can include a capillary or a microchannel and wherein the phospholipid nanogel can be contained in the capillary or the microchannel.

Also described in various embodiments herein are capillaries that can include a phospholipid nanogel having an amount of 1,2-dimyristoyl-sn-glycero-3-phosphocholine (DMPC); an amount of 1,2-dihexanoyl-sn-glycero-3-phosphocholine (DHPC); and an amount of an exoglycosidase enzyme that can range from about 0.001 µUnits/µL of the phospholipid nanogel to about 250 µUnits/µL of the phospholipid nanogel. The ratio of DMPC to DHPC in the phospholipid nanogel can range from about 2.0 to about 3.0. The exoglycosidase enzyme can be selected from the group of: α1-2 Fucosidase, α1-6 Fucosidase, α1-2 Mannosidase, α1-2,3 Mannosidase, α1-2,3,4,6 Fucosidase, α1-2,3,6 Mannosidase, α1-2,4,6 Fucosidase, α1-2,4,6 Fucosidase O, α1-3,4 Fucosidase, α1-3,4,6 Galactosidase, α1-3,6 Galactosidase, α1-6 Mannosidase, α2-3 Neuraminidase, α2-3 Neuraminidase S, α2-3,6 Neuraminidase, α2-3,6,8 Neuraminidase, α2-3,6,8,9 Neuraminidase, α2-3,6,8,9 Neuraminidase A, α-N-Acetylgalactosaminidase, β1-3 Galactosidase, β1-3,6 Galactosidase, β1-4,6 Galactosidase, β1-3,4 Galactosidase, β1-4 Galactosidase, β1-4 Galactosidase S, β-1-2,3,4,6-N-Acetylglucosaminidase, β-N-Acetylglucosaminidase S, β-N-Acetylhexosaminidase and any combination thereof. The phospholipid nanogel can be temperature responsive. The phospholipid nanogel can be contained in one or more specific regions within the capillary.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 8 shows a table that can demonstrate the effect of substrate on delivery rate[a]. [a]Data are averages (n=3) using 5.4 mM 3'-sialyllactose labeled with 2-aminobenzoic acid and 336 µUnits/µL α2-3,6,8,9 neuraminidase in nanogel at 37° C. [b]Incubation performed with E=0 V/cm after driving the substrate to the center of the fixed enzyme zone. [c]Performed by electrophoresing substrate through the enzyme with E=250 V/cm for multiple forward (F) and reverse (R) passes of: 40 s (20F-10R-10F), 60 s (20F-20R-20R), 100 s ([20E-20R]$_2$-20F), or 200 s ([20F-20R]$_4$-20F-10R-10F). [d]Data are averages of rates at four incubation times.

FIG. 11B can depict the Michaelis-Menten curve generated by plotting the substrate concentration and the rate of product formation for 6'-sialyllactose with 336 µU/µL α2-3,6,8,9 neuraminidase in nanogel. Experimental conditions were as described in FIGS. 4A-4B.

FIG. 12B can depict the Michaelis-Menten curve that is generated by plotting the substrate concentration and the rate of product formation for 3'-sialyllactose with 336 µU/µL α2-3 neuraminidase in nanogel. Experimental conditions were as described in FIGS. 4A-4B.

FIG. 13 shows a table that can demonstrate a summary of Michaelis-Menten parameters[1]. [1]Enzyme concentration was 336 µUnits/µL, all curves were deteremined at substrate=about 0.40, 1.25, 3.4, 5.4, or 7.4 mM substrate in triplicate (5 points per concentration, n=15 rates to determine KM, Vmax). [2]30 s 3-pass incubation (20 s forward-5 s reverse-5 s forward), correlation coefficient for nonlinear fit was 0.996. [3]40 s 3-pass incubation (20 s forward-10 s reverse-10 s forward), correlation coefficient for nonlinear fit was 0.950. [4] 40 s 3-pass incubation (20 s forward-10 s reverse-10 s forward), correlation coefficient for nonlinear fit was 0.961.

DETAILED DESCRIPTION

Figure 1:
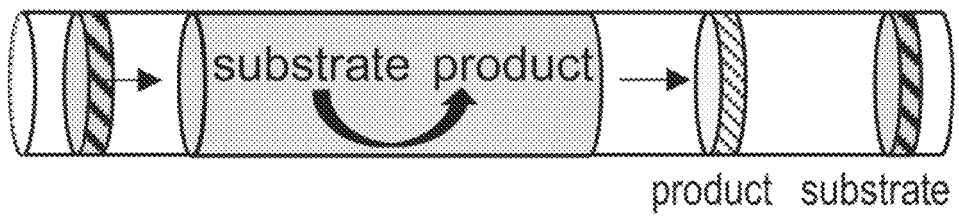
FIG. 1 shows an illustration of embodiments of electrophoretic migration of substrate in-capillary containing enzyme in a fixed zone. The 3'- or 6'-sialyllactose can be incubated in enzyme and converted to lactose. The nonreducing end of the oligosaccharide can be labeled with a chromophore for detection (non-limiting e.g., 2-aminobenzoic acid, for UV-absorbance detection).
Figure 1:
Figure 1:
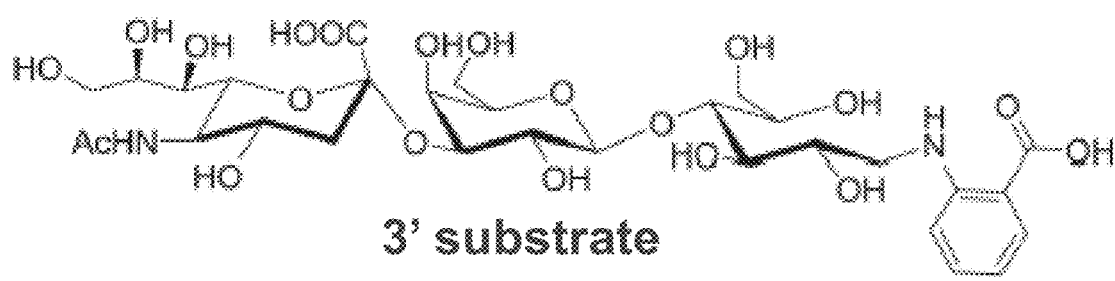
Figure 1:
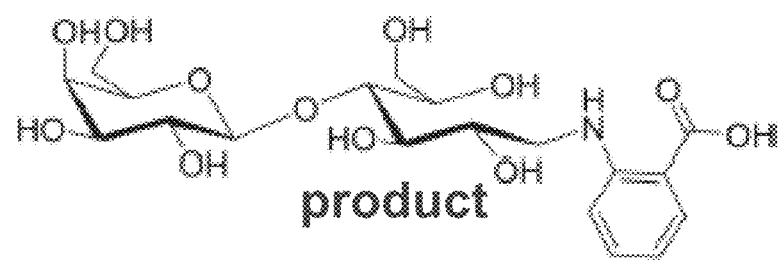
Figure 1:
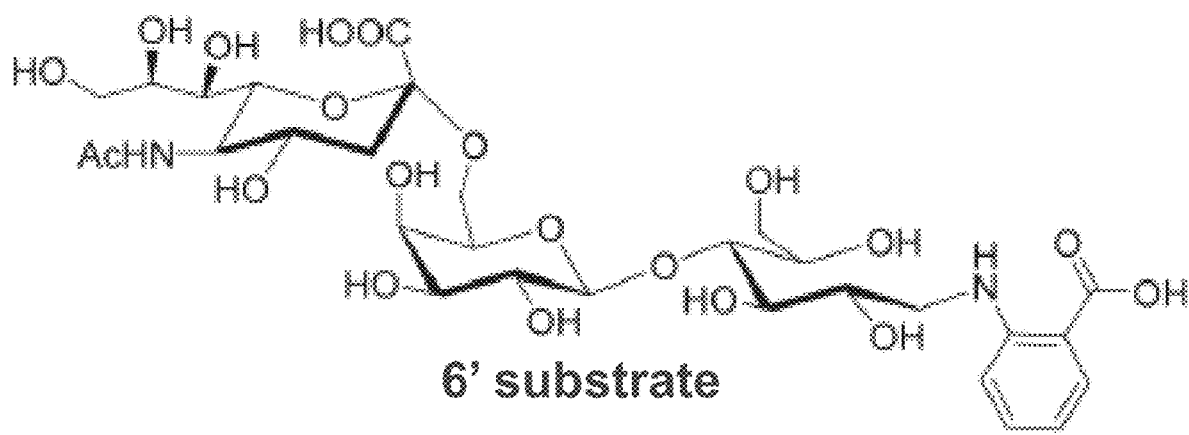

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, chemistry, organic chemistry, biochemistry, and the like, which are within the skill of the art. Such techniques are explained fully in the literature.

Discussion

Exoglycosidase enzymes are commonly used in chemical/molecule based reactions and assays, including those performed in a column, cartridge, or capillary. Immobilization on a substrate such as in a column, cartridge, or capillary can reduce the performance of the exoglycosidase enzyme. Further, exoglycosidase enzymes are unstable at low concentrations in free solution and a drastic loss of enzyme activity occurs even in a buffered solution over time. The current approach to overcome these limitations is to use excess enzyme the column, cartridge, or capillary with enzyme, which can increase the cost of the reactions/assays due to the excess of amount of enzyme needed to be synthesized. Thus, there exists a need for improved methods of restraining susceptible enzymes within a capillary, cartridge, columns, and/or other devices at low concentrations for chemical/molecule based reactions and assays involving exoglycosidase enzymes.

With that said, described herein are phospholipid nanogels that can contain a low amount (i.e. less than about 250 µUnits/µL, but excluding 0 µUnits/µL) of one or more exoglycosidase enzymes. The phospholipid nanogels that can contain a low amount of one or more exoglycosidase enzymes can be included within a column, capillary, microchannel, cartridge or other device and can facilitate physically restraining the exoglycosidase enzyme within the column, capillary, microchannel, cartridge or other device. Thus, also described herein are columns, capillaries, microchannels, cartridges, and other devices that can contain an amount of a phospholipid nanogel that can contain a low amount of one or more exoglycosidase enzymes. Also described herein are methods of using the phospholipid nanogels that can contain a low amount of one or more exoglycosidase enzymes and columns, capillaries, microchannels, cartridges, and other devices that can contain an amount of a phospholipid nanogel that can contain a low amount of one or more exoglycosidase enzymes.

The phospholipid nanogels described herein can have the advantage of allowing the use of low amounts of an exoglycosidase enzyme in a reaction while maintaining the stability and reactivity of the exoglycosidase enzyme. Thus, the phospholipid nanogels can allow lower cost systems and devices to perform in-line assays and reactions involving exoglycosidase enzymes. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Phospholipid Nanogels Containing a Low Amount of an Exoglycosidase Enzyme

The phospholipid nanogels described herein can contain an amount of 1,2-dimyristoyl-sn-glycero-3-phosphocholine (DMPC) and an amount of 1,2-dihexanoyl-sn-glycero-3-phosphocholine (DHPC). Without being bound by theory, the interaction of the phospholipids and the exoglycosidase enzyme(s) in the phospholipid nanogel may stabilize the exoglycosidase enzymes in the phospholipid nanogel (in any state). This can allow for an increased shelf life and reduced cost, inter alia.

The ratio of DMPC to DHPC can range from 2.0 to 3.0. The phospholipid nanogels can also contain a low concentration (i.e. less than about 250 µUnits/µL, but not 0 µUnits/µL) of an exoglycosidase enzyme. As used herein, "about," "approximately," and the like, when used in connection with a numerical variable, can generally refers to the value of the variable and to all values of the variable that are within the experimental error (e.g., within the 95% confidence interval for the mean) or within +/−10% of the indicated value, whichever is greater.

The low concentration of an exoglycosidase enzyme can be any value greater than 0 or about 0.001 to about 0.01, 0.1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 71, 72, 73, 74, 75, 76, 77, 78, 79, 80, 81, 82, 83, 84, 85, 86, 87, 88, 89, 90, 91, 92, 93, 94, 95, 96, 97, 99, 100, 110, 120, 130, 140, 150, 160, 170, 180, 190, 200, 210, 220, 230, 240, 250 µUnits/µL and any other value in between. The exoglycosidase enzyme(s) can each be selected from α1-2 Fucosidase, α1-6 Fucosidase, α1-2 Mannosidase, α1-2,3 Mannosidase, α1-2,3,4,6 Fucosidase, α1-2,3,6 Mannosidase, α1-2,4,6 Fucosidase, α1-2,4,6 Fucosidase O, α1-3,4 Fucosidase, α1-3,4,6 Galactosidase, α1-3,6 Galactosidase, α1-6 Mannosidase, α2-3 Neuraminidase, α2-3 Neuraminidase S, α2-3,6 Neuraminidase, α2-3,6,8 Neuraminidase, α2-3,6,8,9 Neuraminidase, α2-3,6,8,9 Neuraminidase A, α-N-Acetylgalactosaminidase, β1-3 Galactosidase, β1-3,6 Galactosidase, β1-4,6 Galactosidase, β1-3,4 Galactosidase, β1-4 Galactosidase, β1-4 Galactosidase S, β-1-2,3,4,6-N-Acetylglucosaminidase, β-N-Acetylglucosaminidase S, β-N-Acetylhexosaminidase and any combination thereof.

The phospholipid nanogel can be temperature responsive, such that it has a different viscosity at different temperatures. At a temperature range of about 4° C. to up to 23° C., the phospholipid nanogel has a fluid-like viscosity. At a temperature range of 23° C. to about 60° C., the phospholipid nanogel can form a viscous gel. By altering the temperature the phospholipid nanogel can be effectively manipulated, which can facilitate its incorporation into various devices and specific regions therein including, but not limited to, columns, cartridges, capillaries, and microchannels. In some embodiments, the gel phase transition temperature (i.e. the temperature at which the viscosity changes from fluid-like to viscous gel can be about 23° C.

The pH of the phospholipid nanogel described herein can range from 4 to 8, and can include any number therein.

In addition to the phospholipids and the exoglycosidase enzyme, the phospholipid nanogels described herein can further include additional reagents. Such reagents can include, but are not limited to, 5 to 200 mM sodium phosphate, 5 to 200 mM potassium phosphate, 5 to 200 mM citric acid, 5 to 200 mM 2-morpholin-4-ylethanesulfonic acid, 3-(N-Morpholino)propanesulfonic acid, 5 to 200 mM sodium acetate, 5 to 200 mM ammonium acetate, 0.005 to 0.2 mM calcium, 0.005 to 0.2 mM magnesium, 0.001 to 5 mM sodium azide, 0.05 to 10 mM ethylenediaminetetraacetic acid.

The phospholipid nanogels that can contain a low concentration of an exoglycosidase enzyme can be made by any suitable method. The process for making a nanogel as described herein can include weighing out appropriate masses of 1,2-dihexanoyl-sn-glycerol-3-phosphocholine and 1,2-dimyristoyl-sn-glycerol-3-phosphocholine. These phospholipids can be combined with aqueous solution containing the desired buffering reagents and additives at the desired pH value. The components can be mixed until a clear solution with no visible particulate is achieved. The solution can be frozen and then thawed multiple (e.g. from 2 to 4) times. The solution can then be centrifuged at 4 degrees Celsius. The solution can then be stored at cold temperature or it is used. The exoglycosidase can be reconstituted in the nanogel by diluting the enzyme with the nanogel. The exoglycosidase can be purified, and/or concentrated or diluted before it is diluted an incorporated with the nanogel.

Systems Including the Phospholipid Nanogels Containing a Low Amount of an Exoglycosidase Enzyme and Uses Thereof The phospholipid nanogels that can contain a low concentration of an exoglycosidase enzyme can be included in a device such as a column, capillary, microchannel, or a cartridge. The phospholipid nanogel can be included in the device in a specific region or zone within the device. In some embodiments, the phospholipid nanogel can form a plug within the device. In some embodiments, the phospholipid nanogel described herein can be incorporated in a device by first adding it into the device at a temperature below the gel-phase transition temperature. Thus in this state the phospholipid nanogel is in a fluid-like state. In this state, the phospholipid nanogel can be positioned at the desired region within the device. When at the proper position, the temperature of the phospholipid nanogel in the device can be increased to a temperature above the gel-phase transition temperature such that the phospholipid nanogel forms a viscous gel and can become fixed in that position in the device. In this way, the exoglycosidase enzyme can be physically confined to a specific location within a device. Without being bound by theory, the interaction of the phospholipids and the exoglycosidase enzyme(s) in the phospholipid nanogel may stabilize the exoglycosidase enzymes in the phospholipid nanogel (in any state) to allow for the enzyme to be incorporated into a device at low concentrations.

In some embodiments, after inclusion of the phospholipid nanogel into a device it can be used for chemical and molecular reactions. A substrate can then be introduced into the device by any suitable methods or techniques and be brought in contact with the exoglycosidase enzyme(s) contained in the phospholipid nanogel where it can react with the exoglycosidase enzyme(s). Substrates can include, but are not limited to, any substrate of an exoglycosidase. In some embodiments, the substrate can be a(an) disaccharide, oligosaccharide, polysaccharide, N-glycan, O-glycan, glycopeptide, glycoprotein, or any other molecule that contains a saccharide moiety. The products from the reaction with the exoglycosidase enzymes can then be separated, measured, detected, quantified, and/or otherwise analyzed. Movement of the substrate through the device can be by any suitable and/or conventional method such as electrophoretically, osmotically, gravitationally, hydrodynamically, or by diffusion. The substrate can be in any suitable buffer that is compatible with the phospholipid nanogel described herein as well as the other components and/or reagents that can be used with and/or in the columns, cartridges, microchannels, and other devices. An embodiment is shown in FIG. 1. A single exoglycosidase can be reconstituted in nanogel. Multiple exoglycosidases can be reconstituted in nanogel. The nanogel containing the exoglycosidase can be filled in the entire column, cartridge, microchannel or device. The column, cartridge, microchannel and device can be partially filled or completely filled with different combinations of nanogel or nanogel containing single or multiple exoglycosidase enzymes.

Figure 3:
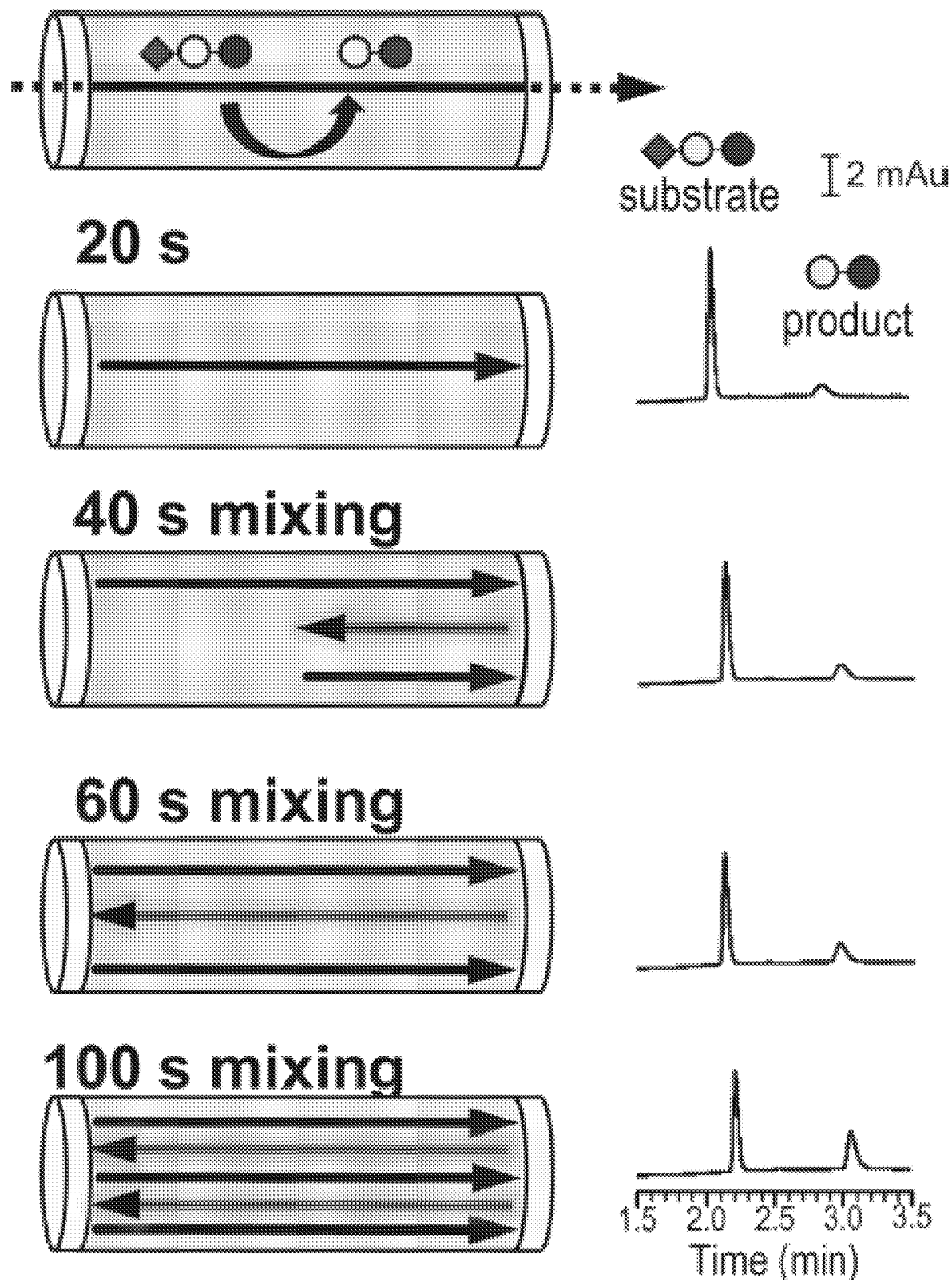
FIG. 3 shows diagrams of multipass electrophoretic mixing for control of the incubation time in the enzyme. The mixing duration can be determined by the total time the substrate passes through the zone. Mixing can include passes of different times that are combined as, for example, in the case of a 40 s incubation. The positions of the arrows in the zone are exemplary and do not imply that the substrate traversed from the top of the zone to the bottom with each successive pass. The electropherograms were obtained using substrate of 5.4 mM 3'-sialyllactose and 336 µUnits/µL of α2-3,6,8,9 neuraminidase that was suspended in phospholipid nanogel. Experimental conditions were as described in FIGS. 2A-2C.

In some embodiments, such as those where the substrate is moved through the device electrophoretically, electrophoretic mixing can be employed. Electorphoretic mixing is a process where the polarity can be periodically switched to result in a change of direction of travel of the substrate to drive the substrate back and forth through the region of the device where the phospholipid gel is located. A conceptual diagram of this is shown in FIG. 3. Mixing can occur for any suitable amount of time. In some embodiments, the mixing can be done for 0, to 10, 20, 30, 40, 50, 60, 70, 80, 90, or 100 s or more. Mixing does not require the substrate to travel the entire length of the phospholipid gel region during mixing or any time within a mixing. Mixing in this manner or other manners that achieve the same or similar passing of the substrate within the region where the phospholipid gel is present can result in improved contact between the substrate and the exoglycosidase enzyme in the phospholipid gel. The time of the mixing and length between switching direction of travel of the substrate can vary as needed based on the specific exoglycosidase enzyme(s) and substrate(s) present.

The phospholipid gels can be used for or included in devices that can be used in a variety of assays and reactions. Such assays and reactions can include, but are not limited to hydrolysis reactions in which exoglycosidase enzymes hydrolyze residues from a(an) disaccharide, oligosaccharide, polysaccharide, N-glycan, O-glycan, glycopeptide, glycoprotein, or any other molecule that contains a saccharide moiety.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction

Sialic acids, the common name for N-acetylneuraminic acids, are the terminal monomer on the nonreducing end of glycans. Sialic acids and enzymes associated with their synthesis or catabolism are involved in a number of cellular processes (1) and are implicated in physiological dysfunctions including cancer, (2-5) antibody function, (6) and inflammation. (7) In proteins, asparagine-linked glycans contain a common core structure, (8) such that can be capped by sialic acids that are adjacent to a galactose residue. These sialic acid-galactose sequences are linked from carbon 2 on the sialic acid to carbon 3 or 6 on the adjacent monomer. The position of this linkage is relevant to cancer, (9) and as a result, the linkage chemistry is monitored. Although there is a critical need for routine sialic acid determinations, the challenges of linkage analysis, isomerization, and data interpretation make structural assignment difficult using current analytical technologies.

Oligosaccharides have been identified using benchtop sequencing with enzymes, but this requires a considerable amount of exoglycosidase and substantial incubation time. (10-14) The cost, stability, and sample preparation related to the use of the enzyme are limiting factors. Ultimately, separation strategies that reduce the sample handling and sample volume are important to consider. Microflow systems can efficiently screen chemical processes, are more stream-lined to develop and optimize reactions, and are used to predict the success of scaling up a method. There are a few barriers to rapidly assessing enzymatic processing on the microscale, which include the cost and lifetime of enzyme preparations. These barriers can be overcome with immobilized enzymes, which can have enhanced performance (15) and have increased stability. Methods of covalent enzyme immobilization require mild derivatization conditions and extensive optimization, and this has led to the development of new strategies to physically confine enzymes without covalent modification. (16, 17) However, these approaches are not without limitations.

To realize the full potential of enzymes in chemical assays, enzymes must be manipulated on the microscale without immobilization. In addition, the rate of enzyme catalysis must be established for different reaction conditions because the enzyme rate is specific for each substrate, and it is dependent upon the conditions used for the enzymatic reaction. Precise knowledge of enzyme activity can be quantified as Michaelis-Menten constants ($K_M$), and it is important to harnessing enzymes for biomolecule recognition, sequencing, and assessment. With this information, enzyme-based microscale analyses have the potential to shed light on the relationship between the biomolecular structure of the substrate and enzyme function. However, new analytical tools are required that stabilize enzyme performance and consume small quantities of enzyme in faster analyses.

Capillary electrophoresis has been adapted to utilize enzymes to improve detection limits and separation specificity with electrophoretically mediated microanalysis, commonly referred to as EMMA. (18) This method relies upon differences in electrophoretic mobility of enzyme, substrate, and product for the analysis. EMMA is rapid, consumes nanoliter volumes of enzyme, and is reported extensively (19-22) as a method to enhance detection limits or provide indirect detection. While not as prevalent, the use of EMMA to determine $K_M$ is feasible if the enzyme remains in the native state, the enzyme does not adsorb to the capillary surface, and the electrophoretic differences of analyte, enzyme, and product facilitate separation. Significant optimization is required to ensure that the incubation conditions are compatible with the electrophoresis, and exquisite strategies to address this optimization have been described. (23-25) These barriers can be overcome with the use of phospholipid nanogels, which self-assemble to form a thermally responsive material that is suitable as a replaceable gel to sieve DNA in capillary electrophoresis, (26, 27) as a viscosity switch to close and open channels in microfluidics, (28, 29) and as a viscous additive to improve capillary electrophoresis separations of oligosaccharides. (30-32) Nanogels can be biocompatible materials that immobilize and pattern enzymes in microscale channels.

This Example can demonstrate an approach to EMMA that utilizes nanogels to physically constrain an enzyme in a separation capillary. Reconstitution of the neuraminidase enzyme in nanogel at low concentration results in a longer lifetime upon storage. This provides a means to cost-effectively use a single enzyme stock solution to deliver the subnanoliter volumes required for the capillary method. An electrophoretic mixing method is developed to circumvent diffusion limitation of static incubation. For the first time, nanogels are harnessed to precisely quantify the Michaelis-Menten constants of an enzyme with different degrees of stereospecificity in the presence of substrates with different linkage positions. The trisaccharide sialyllactose, which is O—(N-acetyl-α-neuraminosyl)-[2→3(or 2→6)]-O-β-d-galactopyranosyl-(1→4)-D-glucose, is used as a model substrate to characterize neuraminidase. The different catalysis rates obtained for sialic acid residues with 2-3 or 2-6 linkages are used to analyze the linkage position of a mixture of 2-3 and 2-6 sialyllactose and in the sialylated triantennary glycan substrate mixture that contained both Galβ(1-3) GlcNAc and Galβ(1-4)GlcNAc. Similar results are achieved when a specific and nonspecific enzyme are used. The approach can extend the nanogel separation method to general as well as specific enzymes.

Materials and Methods

Chemicals. The 3'-sialyllactose and 6'-sialyllactose were from Carbosynth (Berkshire, UK). The phospholipids 1,2-dimyristoyl-sn-glycero-3-phosphocholine (DMPC) and 1,2-dihexanoyl-sn-glycero-3-phosphocholine (DHPC), were from Avanti Polar Lipids (Alabaster, Ala.). Glyko trisialylated, galactosylated, triantennary complex N-glycan was from Prozyme (Hayward, Calif.). Acetic acid was from Fisher Scientific (Pittsburgh, Pa.). Lactose, 3-(N-morpholino)-propanesulfonic acid, 8-aminopyrene-1,3,6-trisulfonic acid, 2-aminobenzoic acid, triethylamine, acetonitrile, methanol, sodium cyanoborohydride, sodium cyanoborohydride (dissolved in tetrahydrofuran), and general neuraminidase (#N-2876) were from Sigma-Aldrich (St. Louis, Mo.). The neuraminidase specific for α2-3 (GE-20 and E-5007) was from QA Bio (Palm Desert, Calif.). Deionized water was from an Elga Purelab ultra water system (Lowell, Mass.).

Preparation and Derivatization of Standards. Enzyme studies with an anticipated $K_M$ in the mM range require that oligosaccharide substrate concentrations in the mM range be used to obtain a Michaelis-Menten curve. For the $K_M$ studies, the substrate was labeled with a chromophore detected by UV-visible absorbance. The chromophore 2-aminobenzoic acid was used as a reagent to label the oligosaccharides as reported previously. (33) The reaction was performed with excess label to ensure 100% labeling efficiency to prevent any bias in the $K_M$ measurement. If the labeling reaction was not complete, then the concentration of the labeled substrate that was UV-absorbing would have been less than the total concentration of substrate (i.e., the combination of labeled and unlabeled substrate) and would confound the measurement of $K_M$. A ratio of 1400 nmol 2-aminobenzoic acid:200 nmol sialyllactose (7:1) was achieved by reacting 1 μL volume of 0.2 M oligosaccharide dissolved in water with 1 μL volume of 1.39 M 2-aminobenzoic acid and 23 μL volume of 1 M sodium cyanoborohydride at 65° C. for 2 h in 0.5 M acetic acid (glacial acetic acid diluted with methanol). Once the reaction was complete, the reaction mixture was evaporated to dryness on a Savant SpeedVac concentrator (Thermo Scientific, Waltham, Mass.). Excess 2-aminobenzoic acid was removed from the labeling reaction using a Discovery DPA-6S solid phase extraction cartridge (50 mg packing material, Supelco, Bellefonte, Pa.) with slight modifications to a previously established literature procedure. (31) Specifically, once the sample was loaded in the extraction cartridge, the 2-aminobenzoic acid was eluted using 10 mL of 95% acetonitrile, 5% aqueous 1 mM triethylamine, and the retained sugars were eluted from the cartridge using 3 mL of aqueous 25 mM triethylamine. To ensure that all of the sialyllactose was labeled and recovered from the purification process, it was compared against a second reaction performed with excess sialyllactose.

To ensure that all of the sialyllactose was labeled and recovered from the purification process, the amount of labeled sialyllactose was compared against that obtained with a second reaction performed with excess sialyllactose (1:50 2-aminobenzoic acid:sialyllactose) with no sample cleanup. The amount of labeled sialyllactose was quantified using the method of standard addition with capillary electrophoresis and UV-visible absorbance detection. Standard addition was accomplished by spiking three equivalent fractions of the 1:50 2-aminobenzoic acid:sialyllactose reaction with three different concentrations (250, 500, 750 μM) of the purified sialyllactose obtained from the 7:1 2-aminobenzoic acid:sialyllactose reaction. To avoid bias due to differences in salt concentration, the samples were introduced with hydrodynamic injections at 3.5 kPa (0.5 psi) for 5 s. A concentration of 500±20 μM was experimentally obtained for a reaction expected to produce 500 μM sialyllactose as it had been reacted at a ratio of 1:50 2-aminobenzoic acid:sialyllactose.

Studies designed to distinguish the linkage position of sialyllactose or glycan were accomplished with substrate concentrations in the nM range. For these linkage position studies the substrate was labeled with a chromophore detected by fluorescence. The fluorescently conjugated oligosaccharides and glycans were labeled as previously described (34) with slight modifications. Glycan labeling was accomplished using 100 mM 8-aminopyrene-1,3,6-trisulfonic acid in 20% acetic acid for a reaction of 7 nmol glycan:250 nmol dye in a total reaction volume of 5 μL. The labeled glycan sample was purified using a 1 kDa molecular weight cutoff filter (#MCP001C41, Pall Corporation, Ann Arbor, Mich.). Sialyllactose labeling was accomplished using 100 mM 8-aminopyrene-1,3,6-trisulfonic acid in 20% acetic acid for a reaction of 5 nmol oligosaccharide:250 nmol dye in a total reaction volume of 5 µL. The labeled sialyllactose samples were purified using the DPA-6S column as described for labeling with 2-aminobenzoic acid. Once purified, the samples were dried in a SpeedVac concentrator before reconstituting to 100 µL in water and storing at −20° C.

Neuraminidase in powder was reconstituted to a concentration of 33.6 mUnits/µL in 50 mM potassium phosphate with the pH adjusted to 5.2 using 1 M sodium hydroxide. The appropriate volume of master stock (i.e., less than or equal to 0.52 µL) was diluted with 10% nanogel to a final volume of 50 µL. For both neuraminidase enzymes, 1 Unit was defined as the amount of enzyme required to produce 1 µmol of methylumbelliferone in 1 min at 37° C., pH 5.0 from 2'-(4-methyl-umbelliferyl)-alpha-d-N acetylneuraminic acid. (35, 36)

Capillary Electrophoresis. Analyses were performed using a P/ACE MDQ or MDQ Plus (Sciex, Redwood City, Calif.) configured by the manufacturer with laser-induced fluorescence detection (3 mW air cooled argon ion laser or 3 mW solid state laser, with $\lambda_{ex}$=488 nm, $\lambda_{em}$=520 nm) and a photodiode array or UV-visible absorbance detector (monitored at 214 nm). A 25 µm internal diameter, 360 µm outer diameter fused silica capillary (Polymicro Technologies, Phoenix, Ariz.) was used for separation. Each day capillaries were prepared as previously reported. (32) Unless otherwise noted, the background electrolyte was 100 mM 3-(N-morpholino)propanesulfonic acid buffered to pH 7. Phospholipids were prepared as described previously, aliquoted, and stored at −20° C. (31, 32, 37) The phospholipid preparation, which was q=2.5 (i.e., [DMPC]:[DHPC]=2.5) and 10% phospholipid by weight, had low viscosity below the gel phase transition temperature and was easily introduced in the capillary at a temperature of 19° C. or lower. Prior to each run, the capillary was held at 19° C. and prepared as previously reported (31) with slight modification.

For Michaelis-Menten analyses, the fixed enzyme zone was introduced at 69 kPa (10 psi) for 7 s followed by injection of background electrolyte at 138 kPa (20 psi) for 15 s. For glycan analyses, this protocol was modified to include a flush of 10% phospholipid at 172 kPa (25 psi) for 3 min prior to loading the nanogel-enzyme zone at 69 kPa (10 psi) for 7 s and background electrolyte at 69 kPa (10 psi) for 45 s. The purpose of the 45 s introduction of background electrolyte was to push the enzyme to the thermostable region of the capillary. The amount of enzyme in the nanogel required for the separation is 15 µL if a PCR vial is used, or 5 µL if lower volume vials from the instrument manufacturer are used (Sciex nanovials product number 5043467). After the capillary was filled, the temperature of the separation was increased to 37° C. for the sample injection, incubation, and separation. Injections included a background electrolyte pre-plug of 6.9 kPa (1.0 psi) for 7 s and a background electrolyte post-plug of 3.4 kPa (0.5 psi) for 5 s. After a run was complete, a 172 kPa (25 psi) background electrolyte flush for five min was applied in the reverse direction to push out any remaining protein toward the site of injection. Ambient thermal control of the room and instrument was maintained using a portable air conditioner described previously. (30)

Data collection and analysis were performed using 32 Karat Software version 7.0 (MDQ) or 10.2 (MDQ Plus). The Michaelis-Menten curves were fit using GraphPad Prism version 4.03 (San Diego, Calif.).

Results

Figure 9:
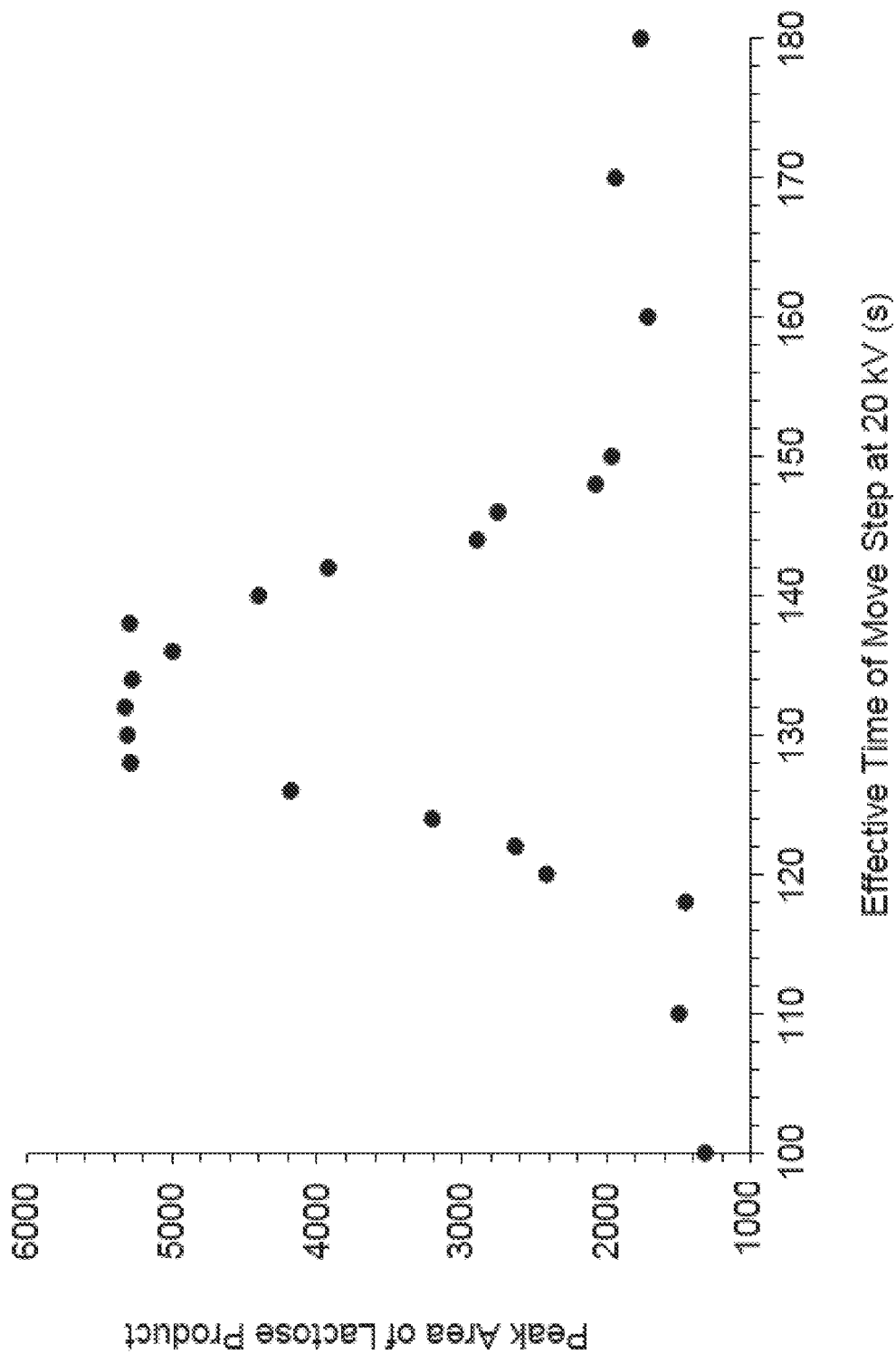
FIG. 9 shows a graph that can demonstrate the use of 3.4 mM 3'-sialyllactose to identify the beginning and end of the fixed enzyme zone. In each study the substrate was electrokinetically migrated into the capillary and incubated for 30 seconds (37° C.) in 336 µUnits/µL α2-3,6,8,9 neuraminidase suspended in phospholipid nanogel. The position was changed and the amount of product generated quantified. Experimental conditions are as described in FIGS. 2A-2C.

Patterning Enzyme in Capillary. The nanogel fixed enzyme zone was achieved by creating a pseudostationary enzyme plug in phospholipid nanogel, as depicted in FIG. 1. Enzyme prepared in the nanogel was introduced into the capillary at about 19° C., which was a temperature that maintained fluid-like viscosity of the material. (28, 29) At this temperature, the enzyme was positioned in the thermally controlled region of the capillary to ensure that the desired temperature was maintained during analyses. The temperature was then increased to about 37° C. to form a viscous gel (28) that maintained the enzyme position within the capillary and supported the enzyme reaction. Two model substrates, sialyllactose with different linkages shown in FIG. 1, were used. Once the fixed enzyme zone was patterned in the capillary, as seen in FIG. 1, the substrate was electrokinetically driven into the enzyme zone. Following incubation, substrate was then separated from product (FIG. 1). The catalysis rate of neuraminidase was quantified by monitoring the conversion of substrate to the lactose product (FIG. 1). The separation of sialyllactose and lactose did not require the use of phospholipid nanogel to resolve these analyte peaks. Therefore, the fixed enzyme zone was embedded in an aqueous solution of about 100 mM of background electrolyte buffered to pH 7. The position of the enzyme zone within the capillary was established by migrating the substrate to a particular position, incubating substrate with enzyme, and then separating and quantifying the peak areas of the substrate and enzymatically generated product. The substrate positions that generated larger product peak area coincided with the position of the enzyme zone, as summarized in FIG. 9. With the position of the enzyme zone established, the impact of nanogel on the enzyme catalysis rate was determined.

Effect of Phospholipid Nanogel on Enzyme Performance. Proteins can be reconstituted in a variety of additives to maintain structure and function (38-41) These additives can influence both stability and activity in a complex manner. (42) Phospholipids can interact with proteins through different mechanisms. (43) Physical constraint of enzymes with lipids has been reported using edge stabilized phospholipid nanodiscs to study enzyme catalysis of membrane protein. (44, 45) Although phospholipids are used to eliminate nonspecific adsorption of proteins to surfaces, (46-48) they are underexplored as an additive for soluble proteins.

Figure 2A:
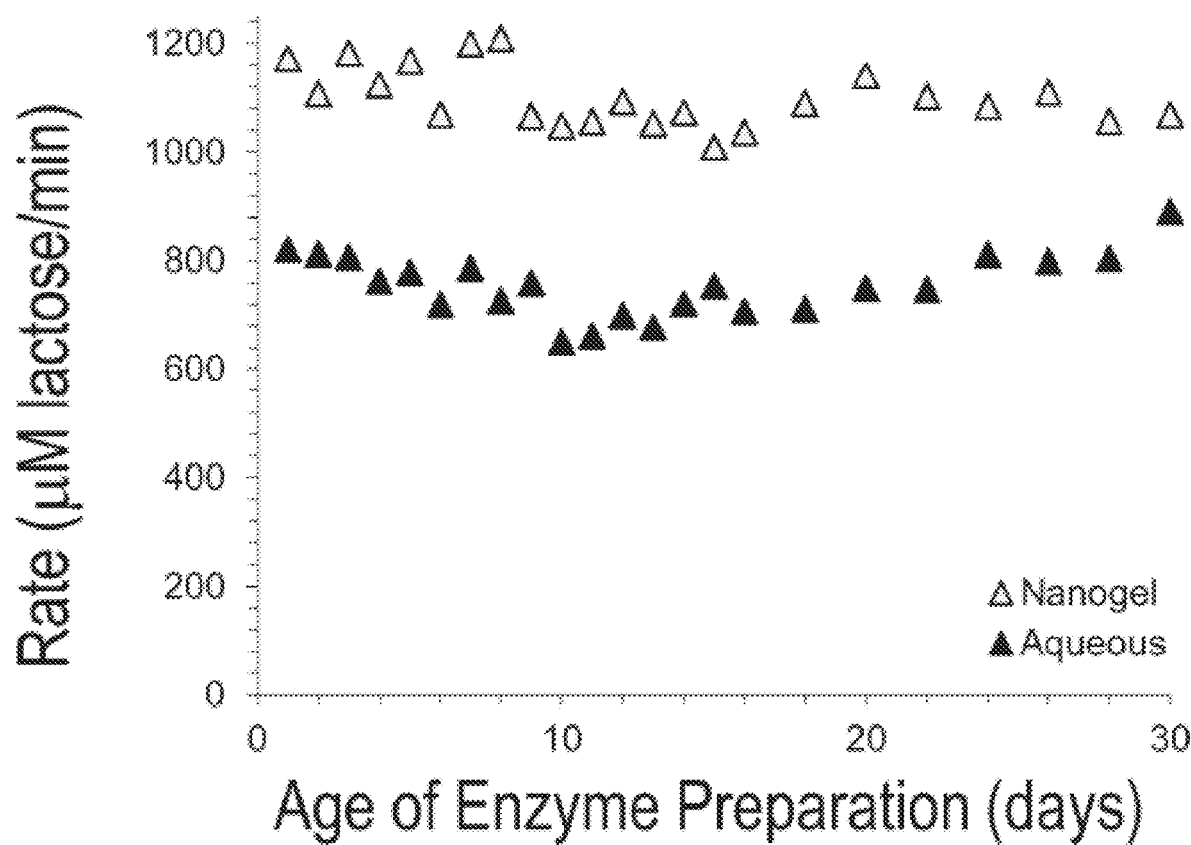
FIGS. 2A-2C show graphs that can demonstrate enzyme activity. Substrate was incubated in α2-3,6,8,9 neuraminidase suspended in phospholipid nanogel (about 10% lipid with [DMPC]/[DHPC]=2.5 in 50 mM potassium phosphate pH adjusted to 5.2 with sodium hydroxide) or in the same aqueous solution devoid of phospholipid at an enzyme concentration of 350 µUnits/µL (FIG. 2A), 250 µUnits/µL (FIG. 2B), and 150 µUnits/µL (FIG. 2C). Substrate (5.4 mM 3'-sialyllactose) was incubated in enzyme for 2 min at 37° C. and separated. Separations were performed at 37° C. in a 25 µm i.d. capillary, with an effective length of 30 cm and E=500 V/cm (reverse polarity).
Figure 2B:
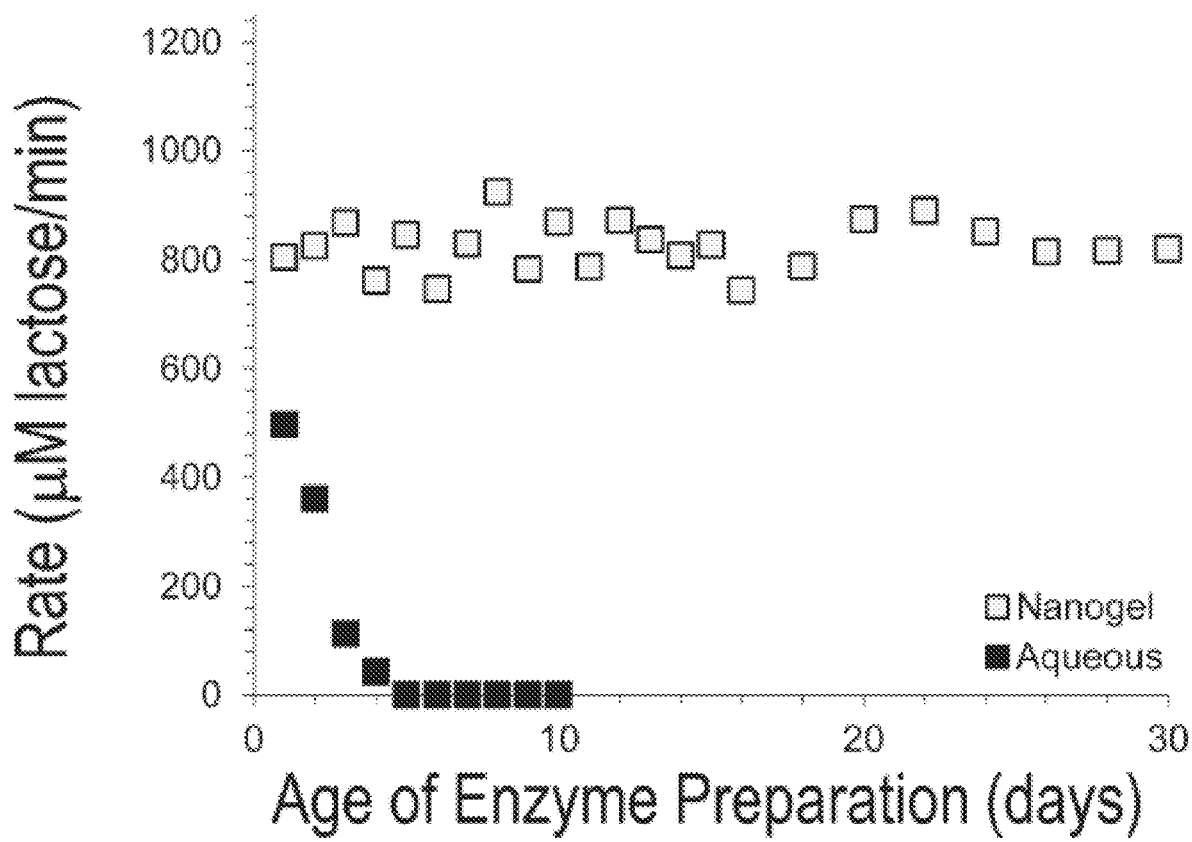
Figure 2C:
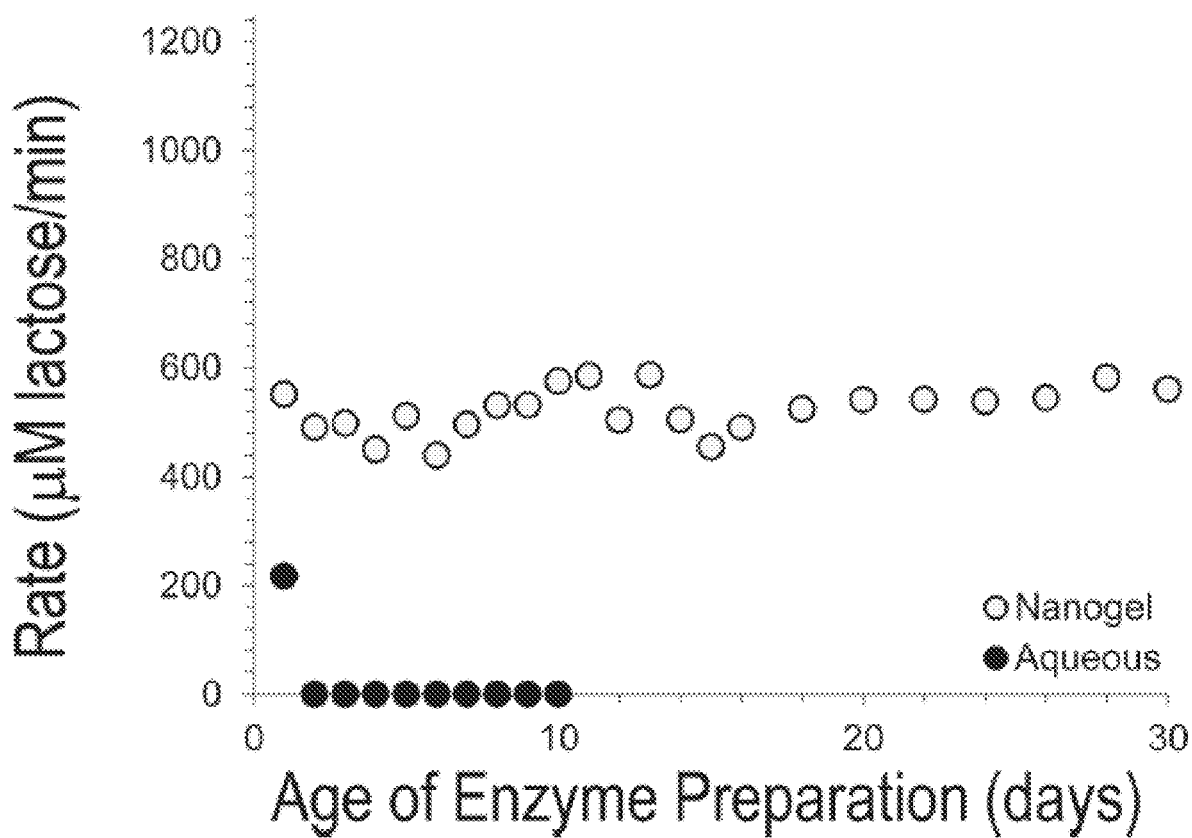

To evaluate the effect of phospholipid nanogel on neuraminidase, the enzyme performance was monitored either in a traditional aqueous solution of about 50 mM potassium phosphate adjusted to a pH of 5.2 with sodium hydroxide or in nanogel comprised of phospholipid dissolved in the same aqueous solution. The preparations of neuraminidase were diluted to a concentration of about 350, about 250, or about 150 µUnits/µL, and the enzyme activity was evaluated by quantifying the rate of conversion of sialyllactose substrate to lactose. The rates summarized in FIGS. 2A-2C can demonstrate that in the presence of nanogel the enzyme retained high activity for the 30-day period regardless of concentration. The stability of the enzyme diluted in the aqueous buffer was concentration-dependent. The 350 µUnits/µL did not change (FIG. 2A). However, the 250 µUnits/µL (FIG. 2B) and 150 µUnits/µL (FIG. 2C) enzyme solutions decreased in activity until there was no detectable activity on days 3 and 1, respectively. The reaction velocity of 350, 250, and 150 µUnits/µL enzyme was 1100±50, 830±50, and 500±40, respectively. At the highest concentration of 350 µUnits/µL, the reaction velocity in nanogel was observed to be about 1.5 times higher than the reaction velocity in aqueous electrolyte (750±60 µM lactose/min). For the lower enzyme concentrations, the reaction velocity in nanogel as compared to that obtained in aqueous electrolyte on day 1 was observed to be 1.7 (500±10 µM lactose/min) and 2.5 (200±10 µM lactose/min) times higher. These findings were in agreement with literature evidence that lipid monolayers improve the performance of exoglycosidase enzymes, including galactosidase (49-51) and neuraminidase. (52). Without being bound by theory, the improvement in stability observed at the lower enzyme concentration may be due to molecular crowding. The compaction of the enzyme by molecules in the solution maintained enzyme in a folded state and impacted the enzyme rate if the effective concentration of active protein was increased (53, 54).

Figure 10:
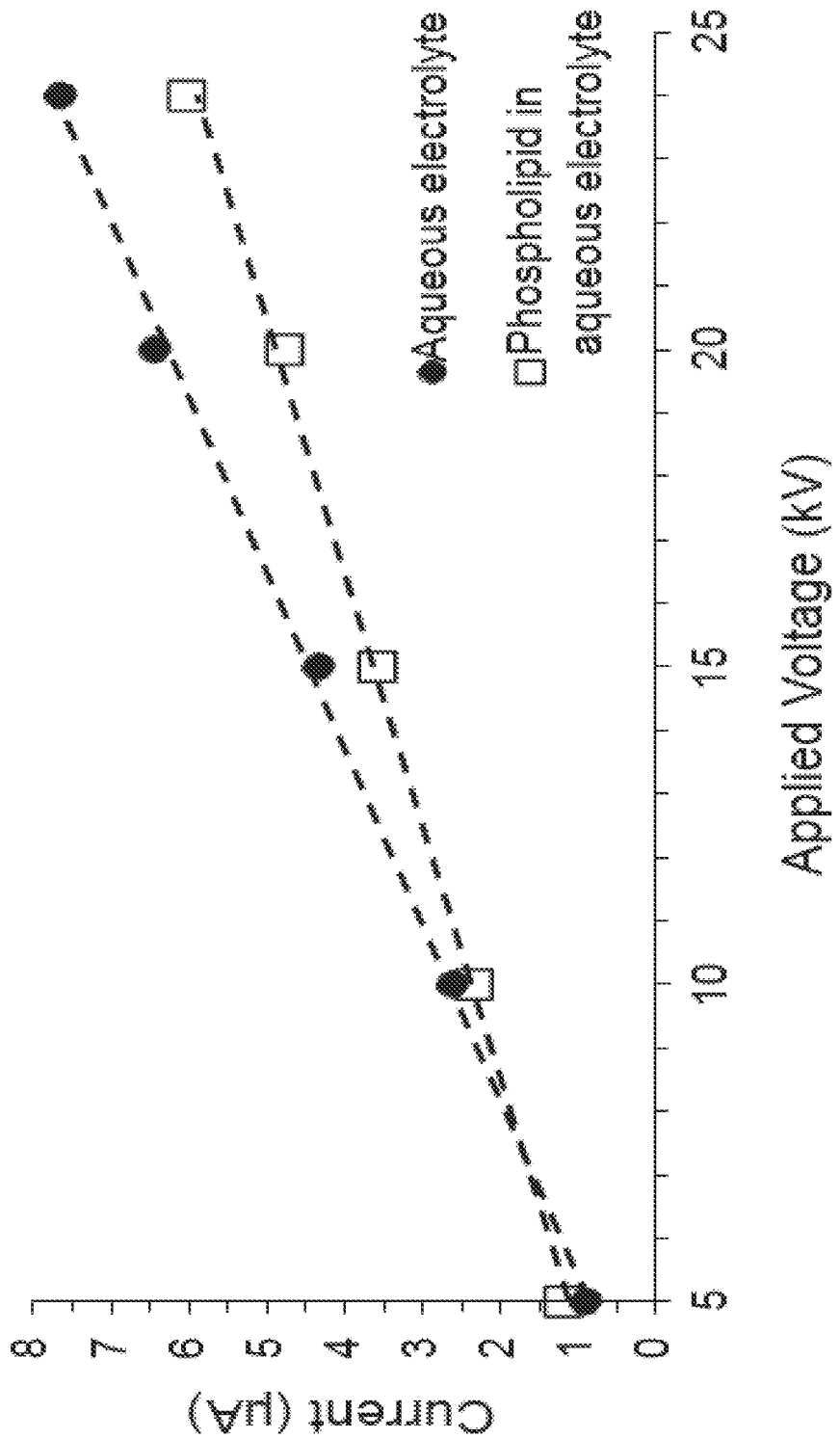
FIG. 10 shows a graph that can demonstrate an Ohm's Law plot. The current can be measured as a function of applied voltage for 40 minutes. The average current (6 to 40 min) can be plotted against the applied voltage and fit using linear regression. The correlation coefficient was 0.998 for aqueous background electrolyte and 0.997 for phospholipid nanogel. All separations were performed at 37° C. in a 25 µm i.d. capillary, with an effective length of 30 cm for buffer and 50 cm for phospholipid.

Optimizing Incubation Times in the Fixed Enzyme Zone. When enzyme catalysis was performed in-capillary using static incubations, the measured velocity (FIG. 8) decreased with increasing incubation time. This diffusion-limited interaction between substrate and enzyme hindered the quantitative determination of enzyme performance as measured by $K_M$ values because enzyme rates must be consistent regardless of incubation time. In nanogel electrophoresis, the limitations of diffusion-based transport of substrate and product were overcome by electrophoretic mixing. In this electrophoretic mixing approach, the sustained contact between substrate and enzyme was achieved by alternating the polarity of the applied voltage to reversibly drive the substrate through the enzyme zone as depicted in FIG. 3. The number of passes and length of each pass were selected to achieve the desired incubation time. The process of mixing in the fixed zone was feasible when the position of the enzyme was profiled in the capillary to determine the zone boundaries as summarized in FIG. 9. The rate of enzyme catalysis increased with the electrophoretic velocity due to the increased probability of enzyme-substrate collision. An Ohm's law plot was performed (FIG. 10) to confirm that this was not due to Joule heating. As summarized in FIG. 8, electrophoretic mixing generated catalysis with a precision of 9% relative standard deviation for four different electrophoretic sweep times as compared to 30% relative standard deviation for four different static incubation times.

Determination of Michaelis-Menten Constants for Neuraminidase. The in-capillary enzymatic method was well-suited to characterize the relationship between the substrate concentration and the performance of the rate of enzyme production. The velocity of product formation was calculated as product concentration/incubation time and then plotted to determine the Michaelis-Menten constant. An accurate measurement of enzyme performance required that the classical rules derived for $K_M$ determinations were followed. (55) In particular, no more than 10% of the substrate could be converted to product because the presence of product inhibits the rate of reaction. An additional consideration was that the amount of product formed must fall within the linear range of quantification for the method of detection. A $K_M$ curve fit using nonlinear regression utilized 2 points at or near saturation and an additional 3 points distributed across the region where the velocity changes significantly with substrate concentration.

Figure 4B:
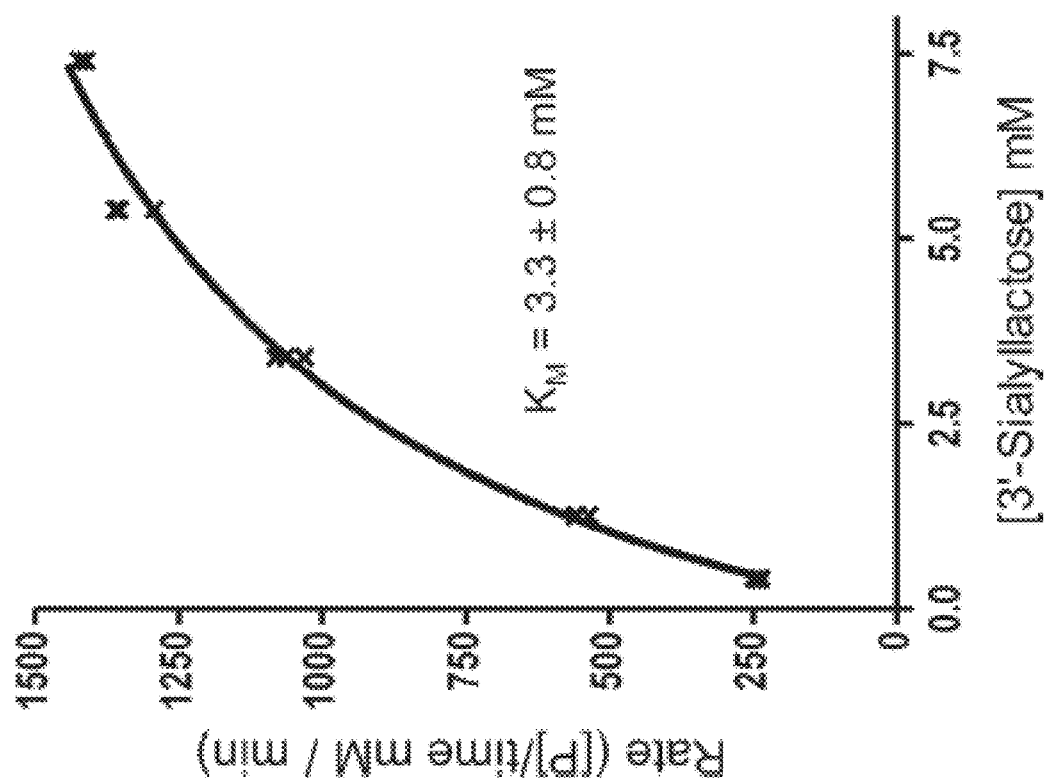
FIGS. 4A-4B shows (FIG. 4A) electropherograms of 3'-sialyllactose substrate and the lactose product generated after enzymatic reaction and corresponding Michaelis-Menten Curve (FIG. 4B). The traces shown in FIG. 4A were offset in time by 0.1 min for visualization from the lower to upper traces at the following 3'-sialyllactose concentrations: 0.40 mM, 1.25 mM, 3.4 mM, 5.4 mM, and 7.4 mM. The increase in the area of lactose with increasing 3'-sialyllactose concentration is depicted in the inset. The Michaelis-Menten curve (FIG. 4B) was generated by plotting the substrate concentration versus the rate of product formation for 3'-sialyllactose with 336 µUnits/µL α2-3,6,8,9 neuraminidase in nanogel. Experimental conditions were as described in FIGS. 2A-2C.
Figure 4A:
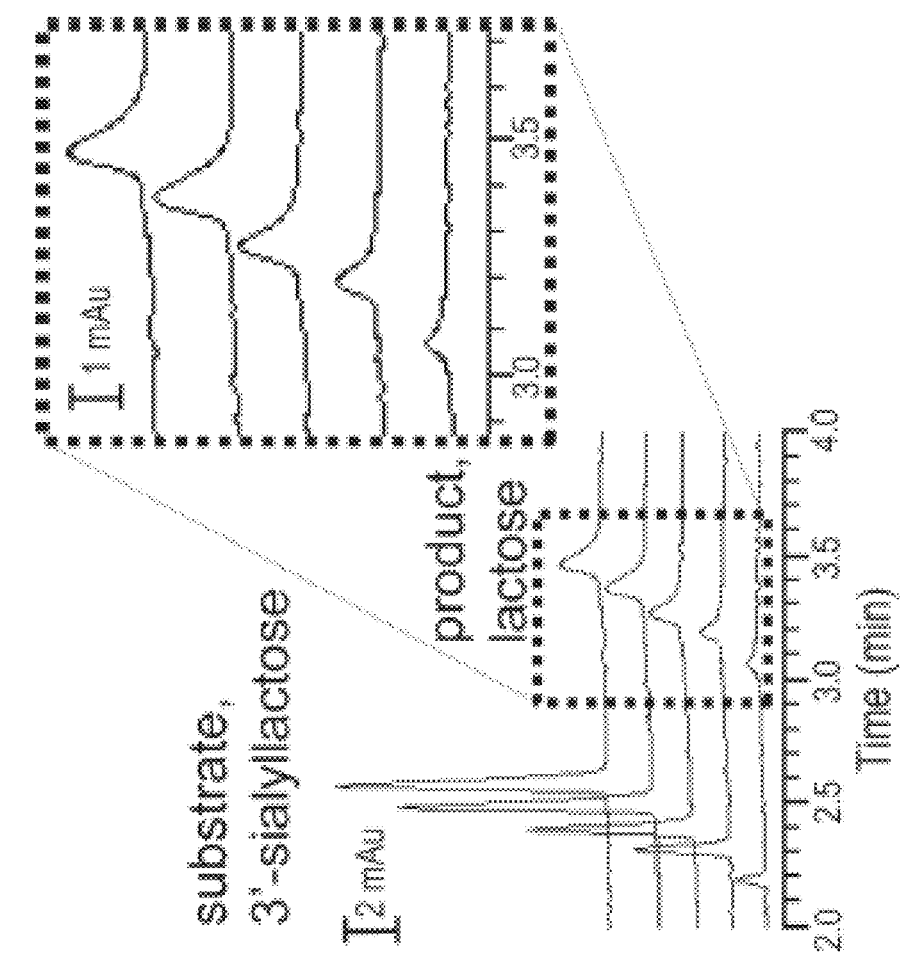

The application of nanogel for in-capillary determination of enzyme activity was demonstrated with a neuraminidase that cleaves sialic acid with an α2-3, 2-6, 2-8, or 2-9 linkage. Each determination utilized nanogel enzymolysis with mixing at an enzyme concentration of 336 µUnits/µL prepared in nanogel. Incubations were performed at 37° C. Electrophoretic mixing was performed during the incubation period to obviate the time-related dependence of velocity on incubation time observed in static incubations. A set of five electropherograms was obtained with 3'-sialyllactose at concentrations of 0.40, 1.25, 3.4, 5.4, and 7.4 mM (FIG. 4A). The peak area for the lactose product obtained in each separation was quantified (FIG. 4A, inset). The rate of enzymatic conversion was calculated as the concentration of lactose produced over the incubation time. These determinations were performed in triplicate; 15 values were plotted as shown in FIG. 4B and fit using nonlinear regression to obtain the $K_M$ of 3.3 mM with a standard deviation of 0.8 mM.

Literature values have been reported for neuraminidase from *Clostridium perfringens* with related sialyllactose substrate. A $K_M$ value of 2.4 with unlabeled 3'-sialyllactose was obtained using potassium acetate buffered at pH 4.5, 37° C., quantifying the product concentration with thiobarbituric-facilitated colorimetric detection with the alkali-Ehrlich method. (56) A $K_M$ value of 2.2±0.3 mM with unlabeled 3'-sialyl-N-acetyllactosamine was obtained using 50 mM potassium phosphate at a pH adjusted to 5.16 with sodium hydroxide, 37° C., quantifying the product with anion exchange chromatography coupled to electrochemical detection. (57) $K_M$ values are difficult to compare given that slight differences exist in the hydrolysis reaction conditions. In addition, the substrate used in this work was labeled with 2-aminobenzoic acid. In light of these differences in reactions, the experimental $K_M$ value was similar, as it was approximately 1.5 times higher than these literature values.

Figure 11A:
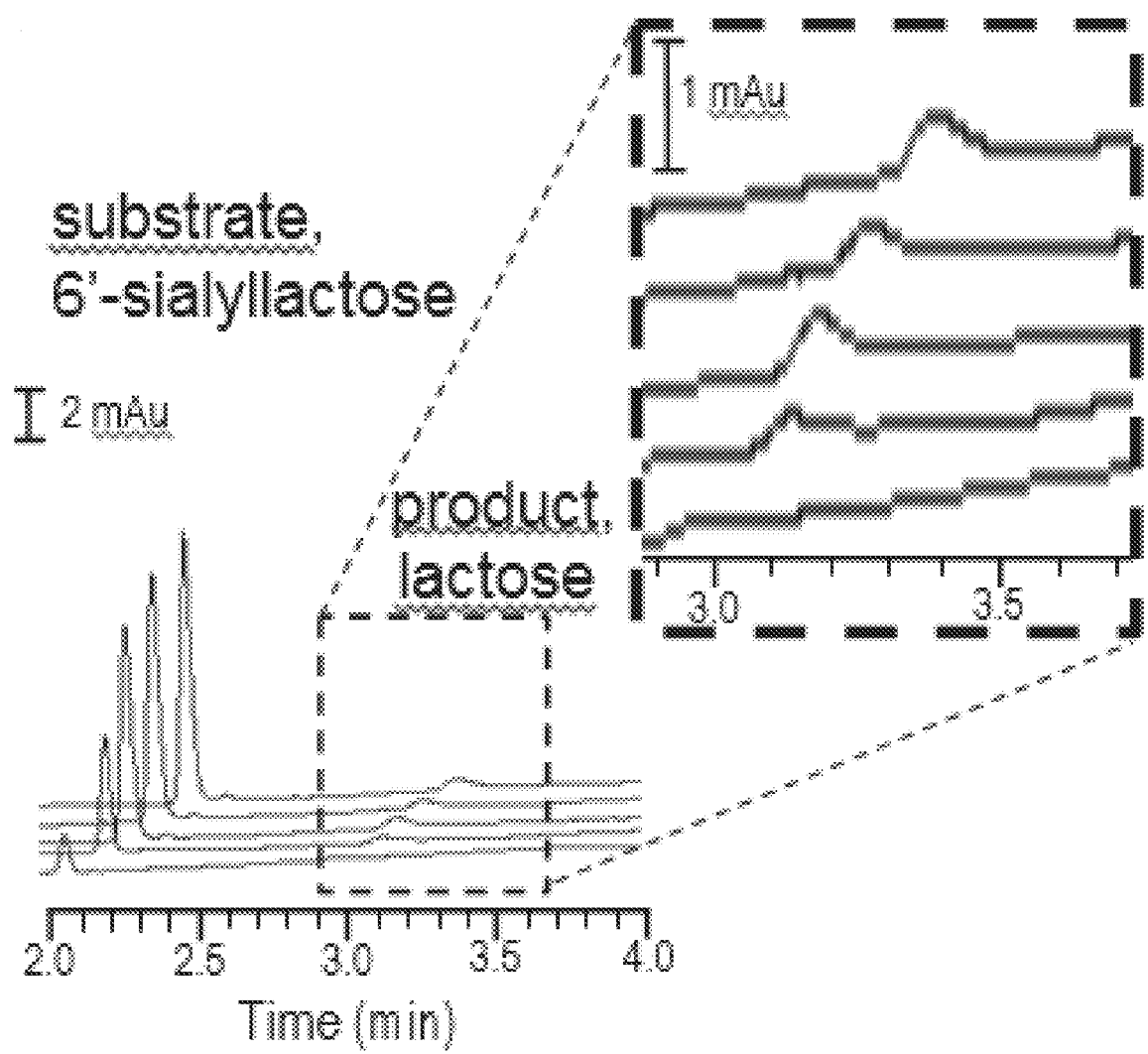
FIGS. 11A-11B show graphs that can (FIG. 11A) depict the separation of 6'-sialyllactose and lactose after enzymatic reaction with 5 different concentrations of 6'-sialyllactose substrate. The traces are offset in time for visualization from the lower to upper traces at the following 3'-sialyllactose concentrations: 0.40 mM (x offset=0 min), 1.25 mM (x offset=0.10 min), 3.4 mM (x offset=0.20 min), 5.4 mM (x offset=0.30 min), and 7.4 mM (x offset=0.40 min). The inset depicts the increase in the area of the lactose product with increasing 3'-sialyllactose concentration.
Figure 11B:
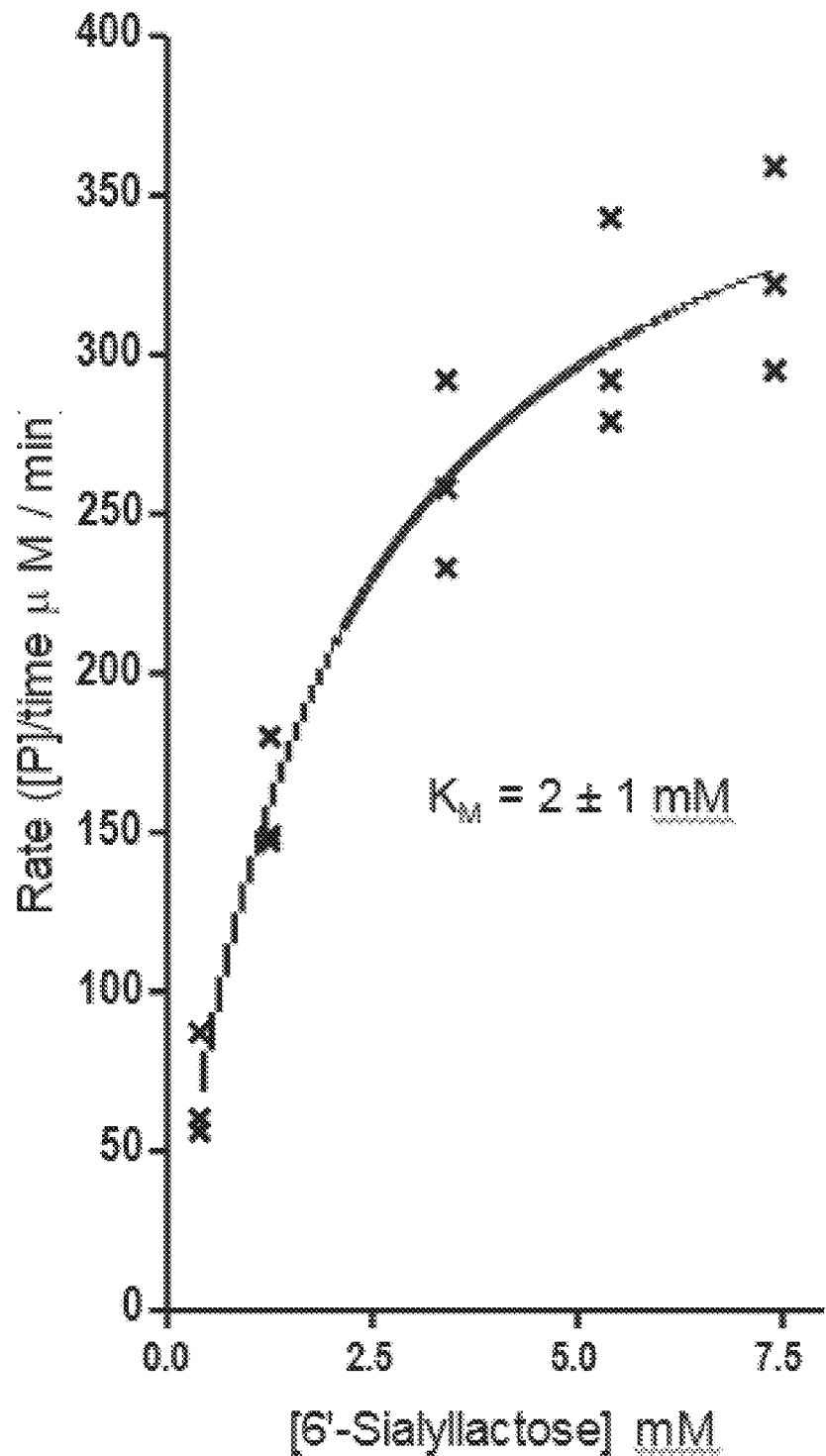
Figure 12A:
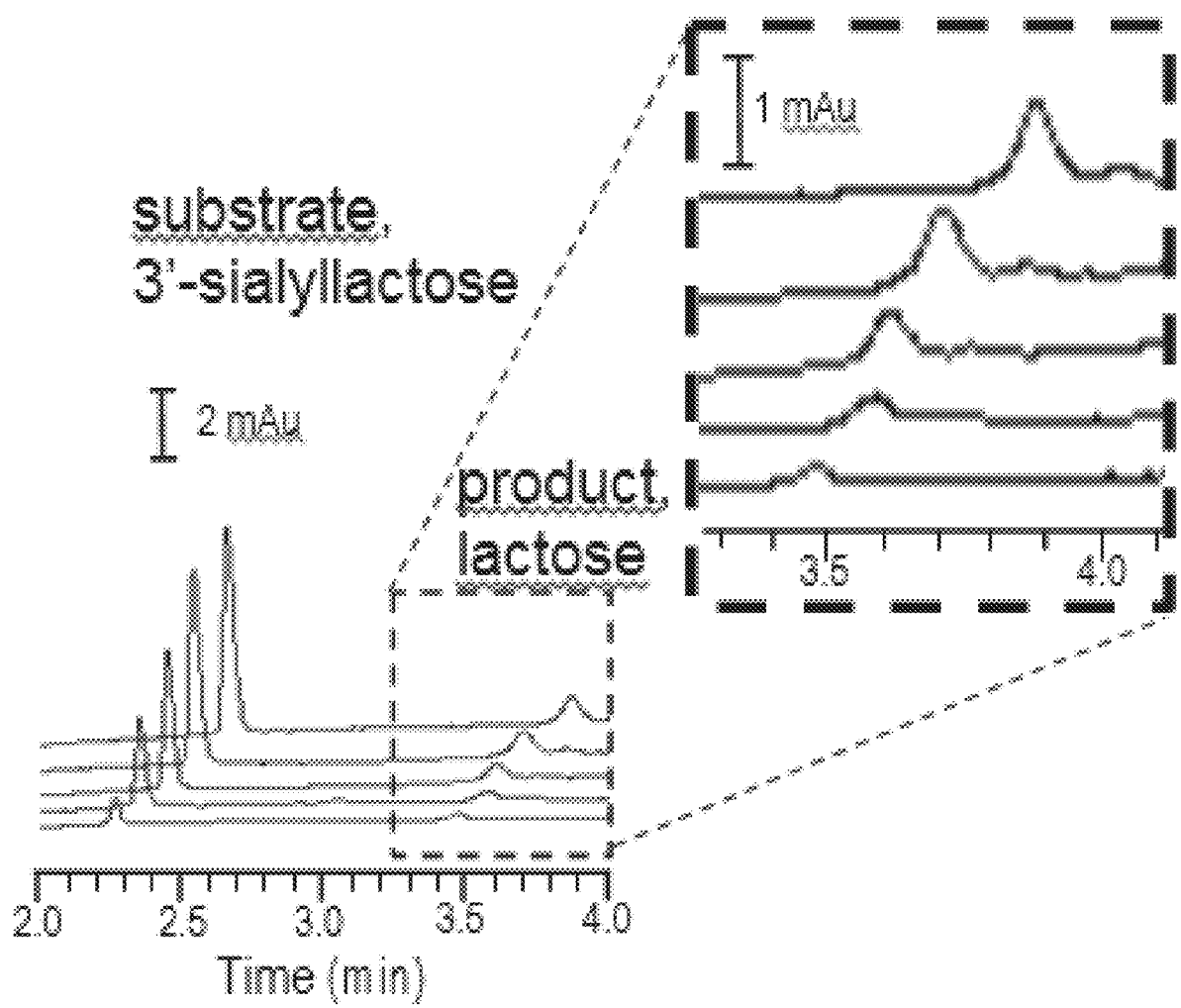
FIGS. 12A-12B show graphs that can depict (FIG. 12A) the separation of 3'-sialyllactose and lactose after enzymatic reaction with 5 different concentrations of 3'-sialyllactose substrate. The traces are offset in time for visualization from the lower to upper traces at the following 3'-sialyllactose concentrations: 0.40 mM (x offset=−0.08 min), 1.25 mM (x offset=0.10 min), 3.4 mM (x offset=0.20 min), 5.4 mM (x offset=0.30 min), and 7.4 mM (x offset=0.35 min). The inset depicts the increase in the area of the lactose product with increasing 3'-sialyllactose concentration.
Figure 12B:
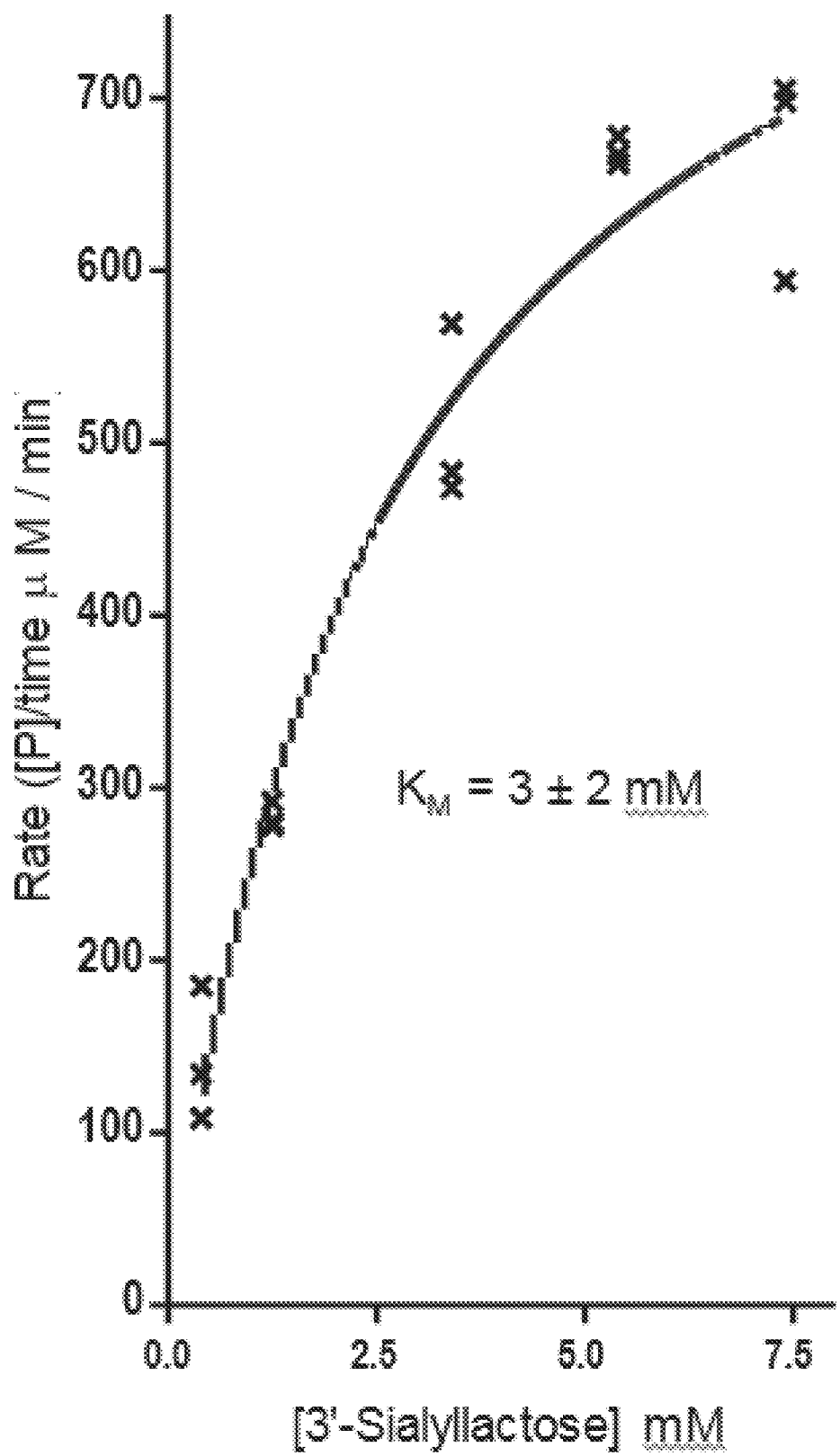

The applicability of nanogel for enzyme characterization was extended to study changes in the rate of catalysis for different substrates and different neuraminidase enzymes. The activity and specificity of α2-3,6,8,9 neuraminidase on 6'-sialyllactose, a substrate with different linkage positions, were examined using the nanogel capillary electrophoresis. The results demonstrated the utility of the method to screen enzymes of different specificity for the conversion of different substrate molecules. The values in FIG. 13 were obtained under identical pH, ionic strength, substrate concentration, and enzyme concentration. The $K_M$ value from the Michaelis-Menten curve for the general neuraminidase acting on 6'-sialyllactose was quantified as 2±1 mM (FIGS. 11A-11B). A similar $K_M$ value of 1.2 mM was reported for general neuraminidase and 6'-sialyllactose with slightly different reaction conditions (i.e., 100 mM sodium/potassium phosphate pH adjusted to 5.4, 37° C.). (58) The $K_M$ value was 3±2 mM for the specific neuraminidase cleaving sialic acid from 3-sialyllactose, as shown in FIGS. 12A-12B. Incubation of the α2-3 neuraminidase with 6'-sialyllactose resulted in no production of lactose, confirming that the specific enzyme was effective at cleaving only 3' sialic acid residues.

The $K_M$ value was independent of enzyme concentration, while $V_{max}$ was dependent upon neuraminidase concentration. Curves were obtained at the same enzyme concentration of 336 µUnits/µL. For this enzyme, the manufacturer reported that the rate was greater for 2-3 than 2-6. (59) The $V_{max}$ values (FIG. 13), which describe the rate of enzyme catalysis when fully saturated by substrate, indicated that the catalytic rate of the general enzyme (e.g., α2-3,6,8,9 neuraminidase) was five times faster for 2-3 substrate when compared to the 2-6 substrate. Furthermore, for conversion of 2-3 sialic acid substrate, the general enzyme was twice as fast as the 3' specific enzyme. These findings were utilized to apply neuraminidase to rapidly distinguish the sialic acid linkage.

Figures 5A, 5B:
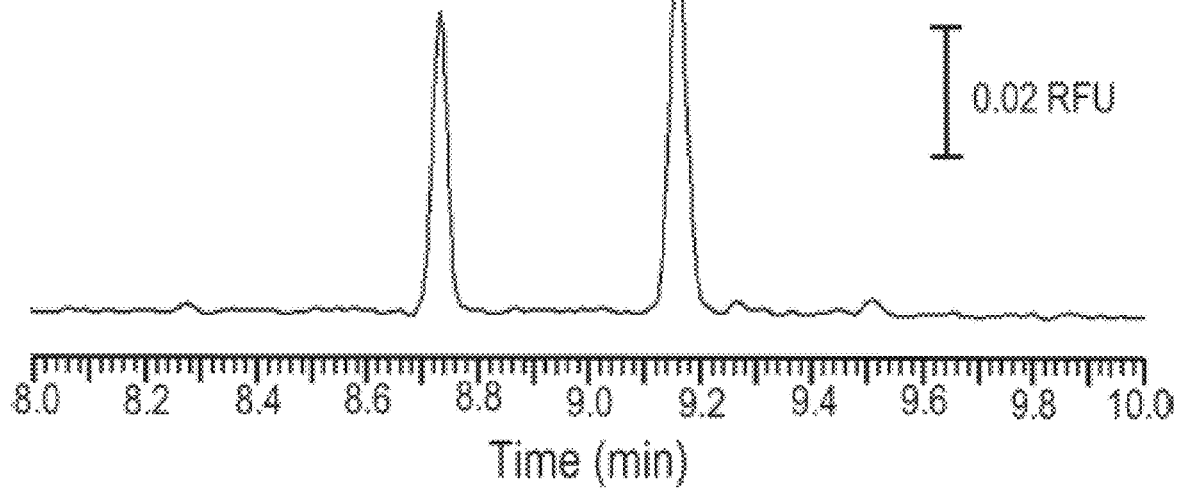
FIGS. 5A and 5B show electropherograms of 3' and 6'-sialyllactose to demonstrate the use of α2-3 neuraminidase to determine substrate linkages. The separation of 3'- and 6'-sialyllactose in the trace of FIG. 5A was obtained in the absence of enzyme. The trace of FIG. 5B incorporated a fixed zone of α2-3 neuraminidase (loaded at 69 kPa for 7 s) suspended in phospholipid nanogel (about 10% lipid with [DMPC]/[DHPC]=2.5 in 50 mM potassium phosphate pH adjusted to 5.2 with sodium hydroxide) at a concentration of 8 mUnits/µL to distinguish 2-3 from 2-6 sialyllactose by cleaving all the sialic acid on the 3'-sialyllactose. Separations and incubations were performed at 37° C. in a 25 µm i.d. capillary filled with nanogel, with an effective length of 50 cm and E=400 V/cm (reverse polarity).
Figures 14A, 14B, 14C:
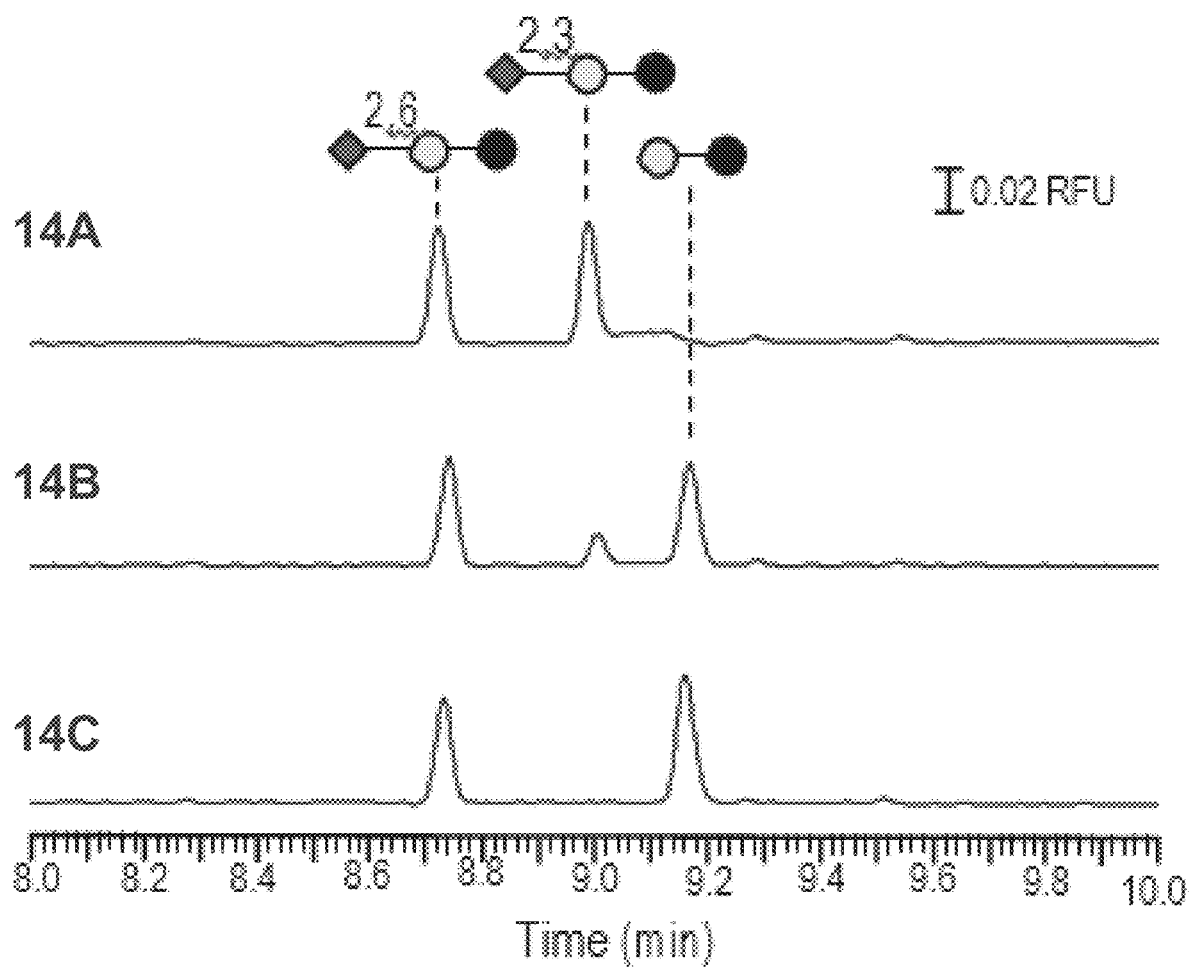
FIGS. 14A-14C show electropherograms of 3'- and 6'-sialyllactose to demonstrate the use of neuraminidase to distinguish 3' and 6' linkages. The 3'- and 6'-sialyllactose peaks were resolved in phospholipid nanogel (10% lipid with [DMPC]/[DHPC]=2.5) devoid of enzyme in trace of FIG. 14A. The 3'-sialyllactose was partially converted to lactose in the presence of α2-3 neuraminidase at a concentration of 0.6 mU/µL in trace of FIG. 14B and entirely converted at a concentration of 8 mU/µL in trace of FIG. 14C. Separations and incubations were performed at 37° C. in a 25 µm i.d. capillary, with an effective length of 50 cm and E=400 V/cm (reverse polarity).

Differentiating the Sialic Acid Linkage with Neuraminidase. With knowledge of the enzyme catalysis, the application of a fixed zone of neuraminidase to distinguish sialyllactose linkage position was demonstrated. A nanogel separation (FIG. 5A, trace A) of the 6' and the 3'-sialyllactose in the absence of enzyme revealed that the 2-6 and the 2-3 sialyllactose linkages were separated. When a mixture of 2-3 and 2-6 sialyllactose was subjected to a fixed enzyme zone of 8 mUnits/μL neuraminidase specific for 2-3 sialic acid linkage, only the 2-3 sialyllactose was converted to lactose (FIG. 5B, trace B). Triplicate runs with and without the fixed enzyme zone generated peaks that had a relative standard deviation in area of 4% and in time of 1%. These studies were performed using fluorescence detection. Data found in FIGS. 14A-14C expanded on these analyses by incorporating a fixed enzyme zone of 0.6 mUnits/μL α2-3 neuraminidase to confirm 3'-sialyllactose was converted to lactose and not just shifted in time.

Figures 6A, 6B:
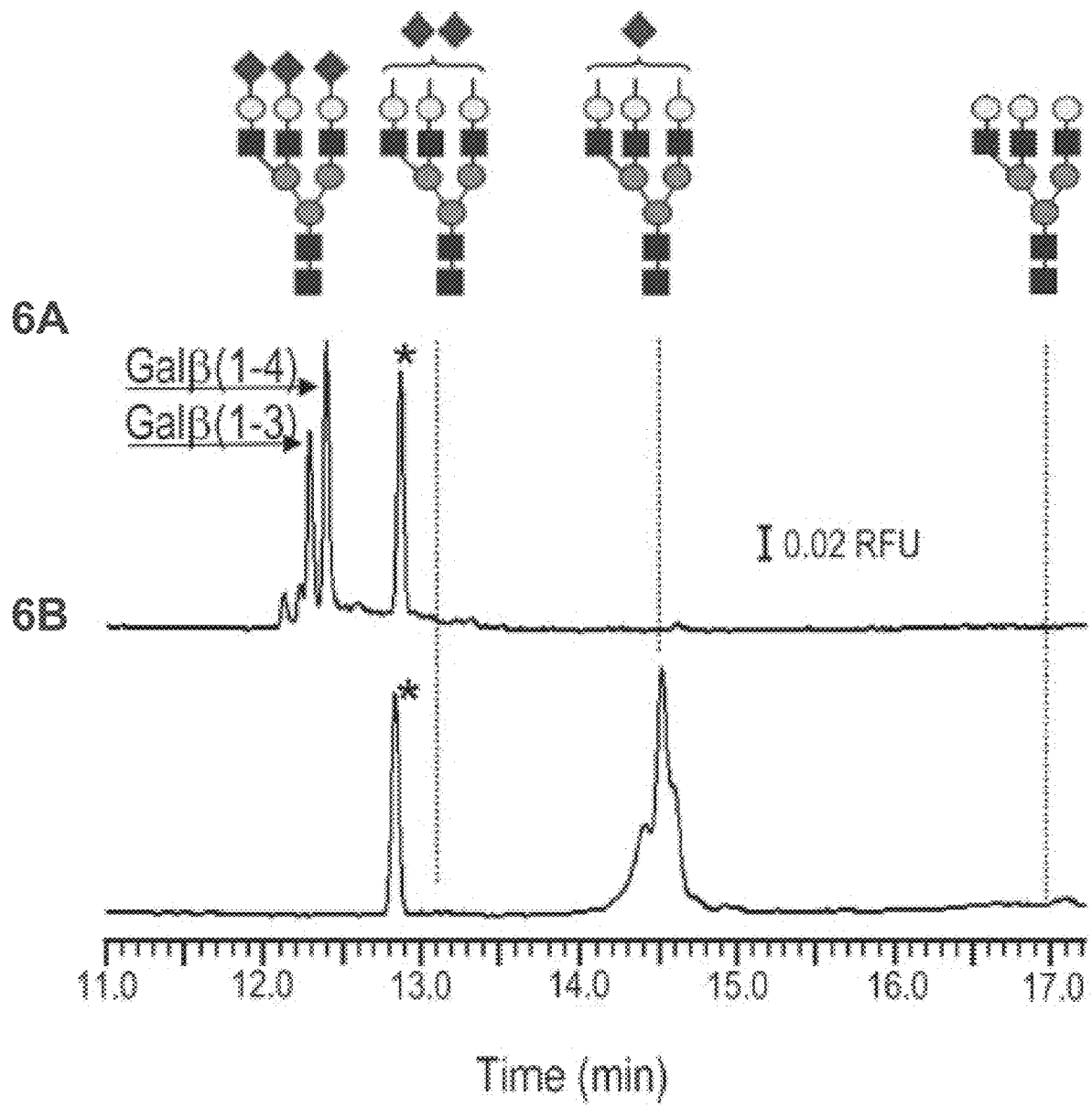
FIGS. 6A-6B show electropherograms of 0.15 nM trisialylated triantennary complex N-glycan incubated in α2-3 neuraminidase to determine linkage position. The trace of FIG. 6A was obtained without enzyme, while the trace FIG. 6B was obtained using about 80 µUnits/µL α2-3 neuraminidase suspended in phospholipid nanogel. The fixed zone of α2-3 neuraminidase (loaded at 69 kPa for 35 s) generated an electropherogram of N-glycan devoid of all 2-3 linked sialic acid. The peak marked with the asterisk was present in the reaction blank. Experimental conditions were the same as those used in FIGS. 5A-5B.

A similar strategy to identify the sialic acid linkage was applied to the mixture of trisialylated triantennary complex N-glycan shown in FIGS. 6A-6B. The N-glycan determinations were accomplished using the fixed nanogel enzyme zone embedded in capillary filled with an enzyme-free nanogel. A nanogel separation (FIG. 6A, trace A) of the N-glycan in the absence of enzyme revealed that the N-glycan was fully sialylated and contained both Galβ(1-3) GlcNAc and Galβ(1-4)GlcNAc. These isomers were resolved electrophoretically when the capillary was filled with nanogel. (30) The separation in FIG. 6B, trace B was obtained with a fixed zone of 80 mUnits/μL α2-3 neuraminidase, resulting in complete cleavage of the 2-3 linked sialic acid. A higher concentration and larger fixed enzyme zone increased the relative standard deviation in area to 11% and in time to 2% (n=3), but was required to desialylate the trisialylated N-glycan. No product peaks were generated that contain two sialic acids. A product peak associated with asialo N-glycan (FIG. 6A, trace A) comprised <1% of the area of the N-glycan peaks. The peaks obtained in these traces indicated that two-thirds of the sialic acid linkages were 2-3, while one-third were 2-6.

Figures 7A, 7B, 7C:
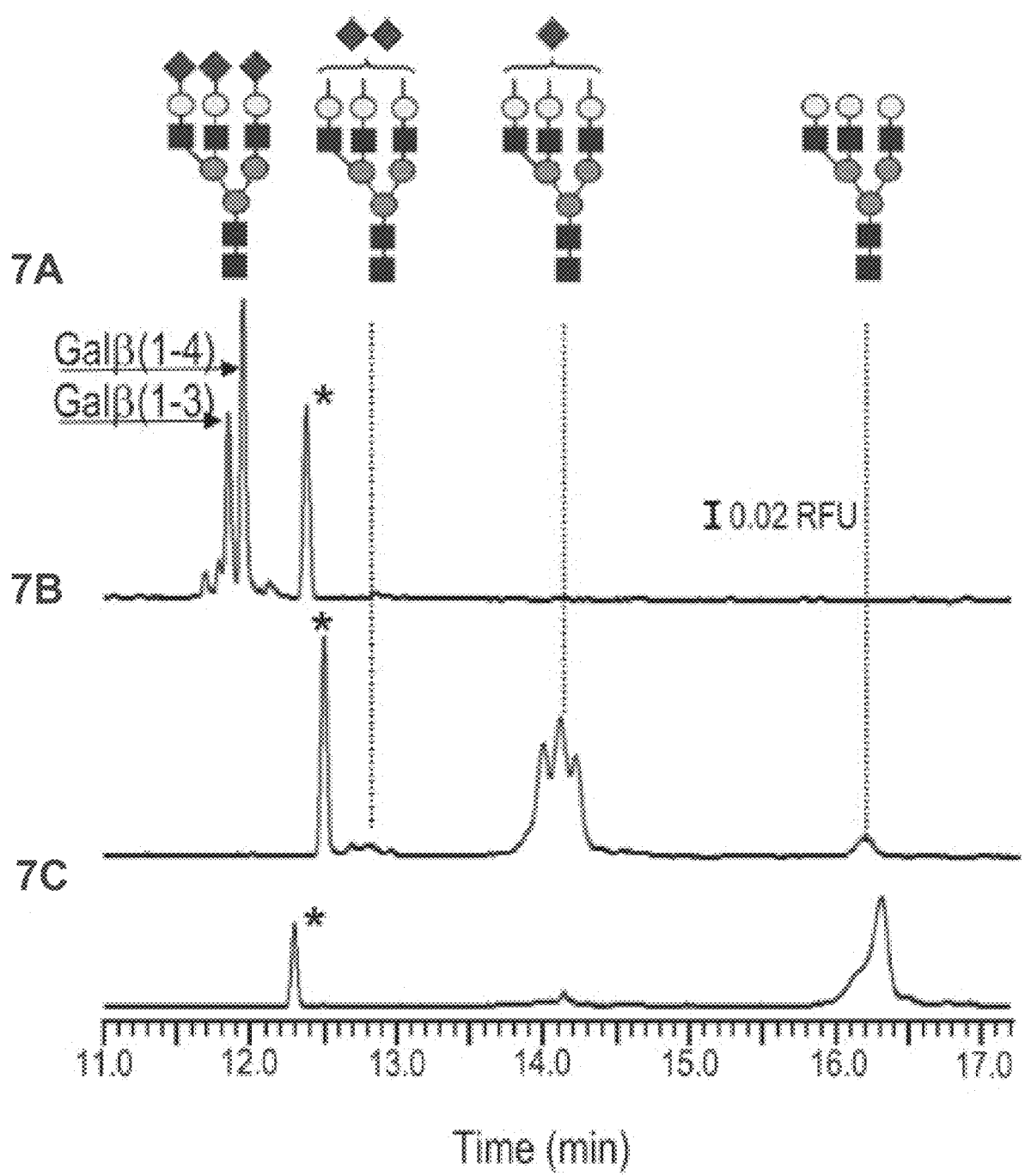
FIGS. 7A-7C show electropherograms of 0.15 nM trisialylated triantennary complex N-glycan incubated in 2-3', 6',8',9' neuraminidase to determine the 3' versus 6' sialic acid composition. The separation in trace of FIG. 7A was obtained in the absence of enzyme. The separation in trace of FIG. 7B was obtained using 4 µUnits/µL α2-3,6,8,9 neuraminidase suspended in phospholipid nanogel (loaded at 69 kPa for 21 s) and generated an electropherogram of N-glycan devoid of all 2-3 linked sialic acid. The fixed zone of 2.4 mUnits/µL α2-3,6,8,9 neuraminidase used in the trace of FIG. 7C (loaded at 69 kPa for 21 s) generated an electropherogram of N-glycan devoid of all sialic acid. The experimental conditions were the same as those used in FIGS. 5A-5B.

To demonstrate that different catalytic rates of general neuraminidase for 2-3 vs 2-6 sialic acid linkages could be harnessed to distinguish linkage position, the experiment was repeated using general neuraminidase. The separation in trace A of FIG. 7A was obtained without enzyme, while the separation in trace B of FIG. 7B was obtained with a fixed enzyme zone of 4 μUnits/μL general neuraminidase. This resulted in complete cleavage of the 2-3 linked sialic acid. Triplicate runs with the fixed zone of general enzyme generated peaks that had a relative standard deviation in area of 10% and in time of 2%. No product peaks were generated that contained two sialic acids. The separation in trace C of FIG. 7C was obtained with a fixed zone of 2.4 mUnits/μL general neuraminidase, resulting in complete cleavage of sialic acid. The same sialic acid linkage composition obtained with specific enzyme was obtained using general enzyme by controlling the concentration of the general neuraminidase.

Summary

Nanogels are a biocompatible separation additive. At a concentration of 150 μUnits/μL, enzyme reconstituted in aqueous electrolyte has a rate that is approximately half of what is obtained when it is reconstituted in nanogel made in the same aqueous solution. Furthermore, when the preparation does not contain nanogel, the activity decreases dramatically at an enzyme concentration of 150 μUnits/μL such that product was not detectable on the second day of measurement. In contrast, neuraminidase reconstituted in nanogel maintained a rate of 500±40 μM lactose/min, as seen in the generation of product measured throughout a 30-day period. A single enzyme stock in nanogel is a cost-effective means to deliver the subnanoliter volumes required for the capillary method.

Nanogel preparations are inexpensive, costing about $0.09 for 5 μL. (60, 61) The nanogel enzyme analyses provide an inexpensive, rapid, and simple means to analyze and quantify the linkage composition of oligosaccharides and are an alternative technology to current methods that rely on derivatization or benchtop digestion. Although the specific enzyme provides greater confidence in the glycan linkage composition, the same information is achievable with the general enzyme that has preferential catalytic specificity for one substrate linkage over another, such as the α2-3,6,8,9 neuraminidase. This is particularly useful in cases where a specific enzyme is not readily available (e.g., α2-8 or α2-9 specific sialidases) or is prohibitively expensive. The method can be harnessed to determine the linkage composition in mixtures of complex N-glycans.

References for Example 1

1. Miyagi, T.; Yamaguchi, K. Glycobiology 2012, 22, 880-896 DOI: 10.1093/glycob/cws057 [Crossref], [PubMed], [CAS]

2. Wang, P.-H. J. Cancer Mol. 2005, 1, 73-81[CAS]

3. Dall'Olio, F.; Malagolini, N.; Trinchera, M.; Chiricolo, M. Front. Biosci., Landmark Ed. 2012, 17, 670-699 DOI: 10.2741/3951 [Crossref], [PubMed], [CAS]

4. Miyagi, T.; Wada, T.; Yamaguchi, K.; Hata, K. Glycoconjugate J. 2004, 20, 189-198 DOI: 10.1023/B:GLYC.0000024250.48506.bf [Crossref], [PubMed], [CAS]

5. Miyagi, T.; Takahashi, K.; Hata, K.; Shiozaki, K.; Yamaguchi, K. Glycoconjugate J. 2012, 29, 567-577 DOI: 10.1007/s10719-012-9394-1 [Crossref], [PubMed], [CAS]

6. Jassal, R.; Jenkins, N.; Charlwood, J.; Camilleri, P.; Jefferis, R.; Lund, J. Biochem. Biophys. Res. Commun. 2001, 286, 243-249 DOI: 10.1006/bbrc.2001.5382 [Crossref], [PubMed], [CAS]

7. Kaneko, Y.; Nimmerjahn, F.; Ravetch, J. V. Science 2006, 313, 670-673 DOI: 10.1126/science.1129594 [Crossref], [PubMed], [CAS]

8. Stanley, P.; Schachter, H.; Taniguchi, N. N-Glycans. In Essentials of Glycobiology, 2nd ed.; Varki, A.; Cummings, R. D.; Esko, J. D.; Freeze, H. H.; Stanley, P.; Bertozzi, C. R.; Hart, G. W.; Etzler, M. E., Eds.; Cold Spring Harbor Laboratory Press: Cold Spring Harbor, N.Y., 2009; Chapter 8, Available from: https://www.ncbi.nlm.nih.gov/books/NBK1917/.

9. Dall'Olio, F.; Trere, D. Eur. J. Histochem 1993, 37, 257-265[PubMed], [CAS]

10. Saldova, R.; Asadi Shehni, A.; Haakensen, V. D.; Steinfeld, I.; Hilliard, M.; Kifer, I.; Helland, A.; Yakhini, Z.; Børresen-Dale, A.-L.; Rudd, P. M. J. Proteome Res. 2014, 13, 2314-2327 DOI: 10.1021/pr401092y [ACS Full Text ACS Full Text], [CAS]

11. Guttman, A.; Ulfelder, K. W. J. Chromatogr. A 1997, 781, 547-554 DOI: 10.1016/S0021-9673(97)00724-3 [Crossref], [PubMed], [CAS]

12. Laroy, W.; Contreras, R.; Callewaert, N. Nat. Protoc. 2006, 1, 397-405 DOI: 10.1038/nprot.2006.60 [Crossref], [PubMed], [CAS]

13. Callewaert, N.; Geysens, S.; Molemans, F.; Contreras, R. Glycobiology 2001, 11, 275-281 DOI: 10.1093/glycob/11.4.275 [Crossref], [PubMed], [CAS]

14. Song, T.; Ozcan, S.; Becker, A.; Lebrilla, C. B. Anal. Chem. 2014, 86, 5661-5666 DOI: 10.1021/ac501102t [ACS Full Text ACS Full Text], [CAS]

15. Szigeti, M.; Bondar, J.; Gjerde, D.; Keresztessy, Z.; Szekrenyes, A.; Guttman, A. J. Chromatogr. B: Anal. Technol. Biomed. Life Sci. 2016, 1032, 139-143 DOI: 10.1016/j.jchromb.2016.02.006 [Crossref], [PubMed], [CAS]

16. Sheldon, R. A. Adv. Synth. Catal. 2007, 349, 1289-1307 DOI: 10.1002/adsc.200700082 [Crossref], [CAS]

17. Brady, D.; Jordaan, J. Biotechnol. Lett. 2009, 31, 1639-1650 DOI: 10.1007/s10529-009-0076-4 [Crossref], [PubMed], [CAS]

18. Bao, J.; Regnier, F. E. J. Chromatogr. A 1992, 608, 217-224 DOI: 10.1016/0021-9673(92)87127-T [Crossref], [PubMed], [CAS]

19. Bao, J. J.; Fujima, J. M.; Danielson, N. D. J. Chromatogr., Biomed. Appl. 1997, 699, 481-497 DOI: 10.1016/S0378-4347(96)00244-7 [Crossref], [PubMed], [CAS]

20. Fan, Y.; Scriba, G. K. E. J. Pharm. Biomed. Anal. 2010, 53, 1076-1090 DOI: 10.1016/j.jpba.2010.04.005 [Crossref], [PubMed], [CAS]

21. Van Dyck, S.; Kaale, E.; Nóvaková, S.; Glatz, Z.; Hoogmartens, J.; Van Schepdael, A. Electrophoresis 2003, 24, 3868-3878 DOI: 10.1002/elps.200305636 [Crossref], [PubMed], [CAS]

22. Nováková, S.; Van Dyck, S.; Van Schepdael, A.; Hoogmartens, J.; Glatz, Z. J. Chromatogr. A 2004, 1032, 173-184 DOI: 10.1016/j.chroma.2003.12.025 [Crossref], [PubMed], [CAS]

23. Montes, R. E.; Gomez, F. A.; Hanrahan, G. Electrophoresis 2008, 29, 375-380 DOI: 10.1002/elps.200700196 [Crossref], [PubMed], [CAS]

24. Riveros, T. A.; Porcasi, L.; Muliadi, S.; Hanrahan, G.; Gomez, F. A. Electrophoresis 2009, 30, 2385-2389 DOI: 10.1002/elps.200800703 [Crossref], [PubMed], [CAS]

25. Montes, R.; Dandouh, F.; Riveros, T. A.; Hanrahan, G.; Gomez, F. A. LC-GC North America 2008, 26, 712-721

26. Durney, B. C.; Lounsbury, J. A.; Poe, B. L.; Landers, J. P.; Holland, L. A. Anal. Chem. 2013, 85, 6617-6625 DOI: 10.1021/ac303745g [ACS Full Text ACS Full Text], [CAS]

27. Durney, B. C.; Bachert, B. A.; Sloane, H. S.; Lukomski, S.; Landers, J. P.; Holland, L. A. Anal. Chim. Acta 2015, 880, 136-144 DOI: 10.1016/j.aca.2015.03.009 [Crossref], [PubMed], [CAS]

28. Pappas, T.; Holland, L. Sens. Actuators, B 2008, 128, 427-434 DOI: 10.1016/j.snb.2007.06.031 [Crossref], [CAS]

29. Wu, X.; Langan, T. J.; Durney, B. C.; Holland, L. A. Electrophoresis 2012, 33, 2674-2681 DOI: 10.1002/elps.201200173 [Crossref], [PubMed], [CAS]

30. Luo, R.; Archer-Hartmann, S. A.; Holland, L. A. Anal. Chem. 2010, 82, 1228-1233 DOI: 10.1021/ac902052m [ACS Full Text ACS Full Text], [CAS]

31. Archer-Hartmann, S. A.; Sargent, L. M.; Lowry, D. T.; Holland, L. A. Anal. Chem. 2011, 83, 2740-2747 DOI: 10.1021/ac103362r [ACS Full Text ACS Full Text], [CAS]

32. Archer-Hartmann, S. A.; Crihfield, C. L.; Holland, L. A. Electrophoresis 2011, 32, 3491-3498 DOI: 10.1002/elps.201100432 [Crossref], [PubMed], [CAS]

33. Sato, K.; Okubo, A.; Yamazaki, S. Anal. Biochem. 1998, 262, 195-197 DOI: 10.1006/abio.1998.2798 [Crossref], [PubMed], [CAS]

34. Váradi, C.; Lew, C.; Guttman, A. Anal. Chem. 2014, 86, 5682-5687 DOI: 10.1021/ac501573g [ACS Full Text ACS Full Text], [CAS]

35. Sigma-Aldrich. Neuraminidase from *Clostridium perfringens* (*C. welchii*)—Type V, lyophilized powder. http://www.sigmaaldrich.com/Graphics/COfAInfo/SigmaSAPQM/COFA/N2/N2876/N2876-BULK_____SLBM0746V_.pdf, accessed Jun. 4, 2016.

36. QAbio. Sialidase Sp. http://www.qa-bio.com/docs/QA-Bio.E-S007.specsheet.pdf, accessed Jun. 4, 2016.

37. Mills, J. O.; Holland, L. A. Electrophoresis 2004, 25, 1237-1242 DOI: 10.1002/elps.200405879 [Crossref], [PubMed], [CAS]

38. Gekko, K.; Timasheff, S. N. Biochemistry 1981, 20, 4667-4676 DOI: 10.1021/bi00519a023 [ACS Full Text ACS Full Text], [CAS]

39. Iyer, P. V.; Ananthanarayan, L. Process Biochem. 2008, 43, 1019-1032 DOI: 10.1016/j.procbio.2008.06.004 [Crossref], [CAS]

40. Chang, B. S.; Mahoney, R. R. Biotechnol. Appl. Biochem. 1995, 22 (Pt 2) 203-214[PubMed], [CAS]

41. Sola-Penna, M.; Meyer-Fernandes, J. R. Arch. Biochem. Biophys. 1998, 360, 10-14 DOI: 10.1006/abbi.1998.0906 [Crossref], [PubMed], [CAS]

42. Shahid, S.; Ahmad, F.; Hassan, M. I.; Islam, A. Arch. Biochem. Biophys. 2015, 584, 42-50 DOI: 10.1016/j.abb.2015.08.015 [Crossref], [PubMed], [CAS]

43. Cserháti, T.; Szögyi, M. Int. J. Biochem. 1991, 23, 131-145 DOI: 10.1016/0020-711X(91)90181-L [Crossref], [PubMed], [CAS]

44. Frank, D. J.; Denisov, I. G.; Sligar, S. G. J. Biol. Chem. 2011, 286, 5540-5545 DOI: 10.1074/jbc.M110.182055 [Crossref], [PubMed], [CAS]

45. Kawai, T.; Caaveiro, J. M.; Abe, R.; Katagiri, T.; Tsumoto, K. FEBS Lett. 2011, 585, 3533-3537 DOI: 10.1016/j.febslet.2011.10.015 [Crossref], [PubMed], [CAS]

46. Cunliffe, J. M.; Baryla, N. E.; Lucy, C. A. Anal. Chem. 2002, 74, 776-783 DOI: 10.1021/ac015627u [ACS Full Text ACS Full Text], [CAS]

47. White, C. M.; Luo, R.; Archer-Hartmann, S. A.; Holland, L. A. Electrophoresis 2007, 28, 3049-3055 DOI: 10.1002/elps.200600816 [Crossref], [PubMed], [CAS]

48. Wells, S. S.; De La Toba, E.; Harrison, C. R. Electrophoresis 2016, 37, 1303-1309 DOI: 10.1002/elps.201600012 [Crossref], [PubMed], [CAS]

49. Sánchez, J. M.; Nolan, V.; Perillo, M. A. Colloids Surf., B 2013, 108, 1-7 DOI: 10.1016/j.colsurfb.2013.02.019 [Crossref], [PubMed], [CAS]

50. Sanchez, J. M.; Perillo, M. A. Colloids Surf., B 2002, 24, 21-31 DOI: 10.1016/S0927-7765(01)00216-8 [Crossref], [CAS]

51. Sanchez, J. M.; Perillo, M. A. Biophys. Chem. 2002, 99, 281-295 DOI: 10.1016/S0301-4622(02)00229-6 [Crossref], [PubMed], [CAS]

52. Perillo, M. A.; Yu, R. K.; Maggio, B. Biochim. Biophys. Acta, Biomembr. 1994, 1193, 155-164 DOI: 10.1016/0005-2736(94)90345-X [Crossref], [PubMed], [CAS]

53. Minton, A. P.; Wilf, J. Biochemistry 1981, 20, 4821-4826 DOI: 10.1021/bi00520a003 [ACS Full Text ACS Full Text], [CAS]

54. Minton, A. P. Biophys. J. 1992, 63, 1090-1100 DOI: 10.1016/S0006-3495(92)81663-6 [Crossref], [PubMed], [CAS]

55. Voet, D.; Voet, J. G. Biochemistry, 4th ed.; John Wiley and Sons: New York, 2010; pp 488-489.

56. Cassidy, J. T.; Jourdian, G. W.; Roseman, S. J. Biol. Chem. 1965, 240, 3501-3506 [PubMed], [CAS]

57. Thobhani, S.; Ember, B.; Siriwardena, A.; Boons, G.-J. J. Am. Chem. Soc. 2003, 125, 7154-7155 DOI: 10.1021/ja029759w [ACS Full Text ACS Full Text], [CAS]

58. Bouwstra, J. B.; Deyl, C. M.; Vliegenthart, J. F. Biol. Chem. Hoppe-Seyler 1987, 368, 269-275 DOI: 10.1515/bchm3.1987.368.1.269 [Crossref], [PubMed], [CAS]

59. Sigma-Aldrich. Neuraminidase from *Clostridium perfringens* (*C. welchii*); http://www.sigmaaldrich.com/catalog/product/sigma/n2876?lang=en&region=US, accessed Jun. 4, 2016.

60. Avanti Polar Lipids, Inc., 06:0 PC (DHPC) 850305. http://avantilipids.com/product/850305/, accessed Jun. 4, 2016.

61. Avanti Polar Lipids, Inc., Product 14:0 PC (DMPC) 850345. http://avantilipids.com/product/850345/, accessed Jun. 4, 2016.

We claim:

1. A phospholipid nanogel comprising:
a lipid comprising 1,2-dimyristoyl-sn-glycero-3-phosphocholine (DMPC) and 1,2-dihexanoyl-sn-glycero-3-phosphocholine (DHPC) with a ratio of DMPC to DHPC that ranges from 2.0 to 3.0, wherein the lipid is in an amount effective to produce a gel transition temperature of about 23° C., wherein the phospholipid nanogel has a fluid-like viscosity at a temperature range from 4° C. to about 23° C., and wherein the phospholipid nanogel forms a viscous gel from about 23° C. to 60° C.;
and an amount of an exoglycosidase enzyme that ranges from about 0.001 µUnits/µL of the phospholipid nanogel to about 250 µUnits/µL of the phospholipid nanogel, and
wherein the pH of the phospholipid nanogel ranges from about 4 to about 8.

2. The phospholipid nanogel of claim 1, wherein the exoglycosidase enzyme can be selected from the group consisting of: α1-2 Fucosidase, α1-6 Fucosidase, α1-2 Mannosidase, α1-2,3 Mannosidase, α1-2,3,4,6 Fucosidase, α1-2,3,6 Mannosidase, α1-2,4,6 Fucosidase, α1-2,4,6 Fucosidase O, α1-3,4 Fucosidase, α1-3,4,6 Galactosidase, α1-3,6 Galactosidase, α1-6 Mannosidase, α2-3 Neuraminidase, α2-3 Neuraminidase S, α2-3,6 Neuraminidase, α2-3,6,8 Neuraminidase, α2-3,6,8,9 Neuraminidase, α2-3,6,8,9 Neuraminidase A, α-N-Acetylgalactosaminidase, β1-3 Galactosidase, β1-3,6 Galactosidase, β1-4,6 Galactosidase, β1-3,4 Galactosidase, β1-4 Galactosidase, β1-4 Galactosidase S, β-1-2,3,4,6-N-Acetylglucosaminidase, β-N-Acetylglucosaminidase S, β-N-Acetylhexosaminidase and any combination thereof.

3. The phospholipid nanogel of claim 1, wherein the phospholipid nanogel further comprises a reagent selected from the group consisting of: sodium phosphate, potassium phosphate, citric acid, 2-morpholin-4-ylethanesulfonic acid, 3-(N-Morpholino)propanesulfonic acid, sodium acetate, ammonium acetate, calcium, magnesium, sodium azide, mM ethylenediaminetetraacetic acid, and any combination thereof.

4. A device comprising:
the phospholipid nanogel of claim 1 contained in a capillary or a microchannel.

5. The phospholipid nanogel of claim 1, wherein the phospholipid nanogel is composed of 10% or more of the lipid by volume.

* * * * *